US009163076B2

(12) United States Patent
Allen-Hoffmann et al.

(10) Patent No.: US 9,163,076 B2
(45) Date of Patent: Oct. 20, 2015

(54) HUMAN SKIN EQUIVALENTS EXPRESSING EXOGENOUS POLYPEPTIDES

(75) Inventors: B. Lynn Allen-Hoffmann, Madison, WI (US); Cathy Ann-Rasmussen Ivarie, Marshall, WI (US); Christina L. Thomas-Virnig, Madison, WI (US)

(73) Assignee: Stratatech Corporation, Madison, WI (US)

( * ) Notice: Subject to any disclaimer, the term of this patent is extended or adjusted under 35 U.S.C. 154(b) by 0 days.

(21) Appl. No.: 11/365,357

(22) Filed: Mar. 1, 2006

(65) Prior Publication Data

US 2006/0257383 A1    Nov. 16, 2006

Related U.S. Application Data

(60) Provisional application No. 60/657,592, filed on Mar. 1, 2005.

(51) Int. Cl.
| *A01N 63/00* | (2006.01) |
| *G01N 33/567* | (2006.01) |
| *C12N 5/07* | (2010.01) |
| *C07K 14/81* | (2006.01) |
| *C12N 5/071* | (2010.01) |
| *A61K 35/12* | (2015.01) |
| *A61K 48/00* | (2006.01) |

(52) U.S. Cl.
CPC .......... *C07K 14/8146* (2013.01); *C12N 5/0629* (2013.01); *A01K 2267/035* (2013.01); *A61K 35/12* (2013.01); *A61K 48/00* (2013.01); *C12N 2501/70* (2013.01); *C12N 2510/00* (2013.01)

(58) Field of Classification Search
CPC .......................... C07K 14/8146; C12N 5/0629
USPC ...................................................... 424/93.21
See application file for complete search history.

(56) References Cited

U.S. PATENT DOCUMENTS

| 6,514,711 | B2 * | 2/2003 | Allen-Hoffmann ......... 435/7.21 |
| 6,562,596 | B1 | 5/2003 | Silbiger et al. |
| 2001/0023061 | A1 | 9/2001 | Allen-Hoffmann et al. |
| 2002/0102726 | A1 | 8/2002 | Allen-Hoffmannq |
| 2002/0142282 | A1 | 10/2002 | Allen-Hoffmann |
| 2002/0164793 | A1 | 11/2002 | Conrad et al. |
| 2002/0168768 | A1 | 11/2002 | Comer et al. |
| 2002/0187498 | A1 | 12/2002 | Comer et al. |
| 2002/0192196 | A1 | 12/2002 | Allen-Hoffmann |
| 2003/0157476 | A1 | 8/2003 | Allen-Hoffmann et al. |
| 2003/0211587 | A1 | 11/2003 | Ariizumi et al. |
| 2004/0146881 | A1 | 7/2004 | Allen-Hoffmann et al. |
| 2004/0235724 | A1 | 11/2004 | Berdel et al. |
| 2004/0265787 | A9 | 12/2004 | Allen-Hoffmann et al. |
| 2005/0079578 | A1 | 4/2005 | Centanni et al. |
| 2005/0186185 | A1 | 8/2005 | Conrad et al. |
| 2005/0226853 | A1 | 10/2005 | Conrad et al. |
| 2006/0030044 | A1 | 2/2006 | Allen-Hoffmann |
| 2006/0121608 | A1 | 6/2006 | Comer et al. |
| 2006/0222635 | A1 | 10/2006 | Centanni et al. |
| 2006/0257383 | A1 | 11/2006 | Allen-Hoffmann et al. |
| 2006/0258001 | A1 | 11/2006 | Allen-Hoffmann et al. |

FOREIGN PATENT DOCUMENTS

| WO | WO 93/18794 A | 9/1993 |
| WO | JP 09 012478 A | 1/1997 |
| WO | 03/093418 | 11/2003 |
| WO | WO 2004/043481 A2 | 5/2004 |
| WO | 2005/012492 | 2/2005 |

OTHER PUBLICATIONS

Salonurmi et al., 2004/2003, Cell Tissue Res. 315:27-37.*
Xue et al., 2006, Expert. Opin. Ther. Targets , 10:143-55.*
Osborne et al., 2002, British Journal of Dermatology146: 26-31.*
Bertaux et al., 1991, J. Invest. Dermatol. 97: 679-685.*
Staggers et al ., 1995, gene 153:297-8.*
Allen Hoffman et al (J. Invest Dermatol. 114:444-455.*
Boukamp et al J, Cell Biol. 106:761-771.*
Hornebeck et al., 2003, Pathologie Biologie 51:569-573.*
Mass-Szabowski et al., 2000, J. Invest. Dermatol. 114:1075-1084.*
Stadelmann W K et al, "Physiology an Healing Dynamics of Chronic Cutaneous Wounds," American Journal of Surgery, Aug. 1998, vol. 176(2A) pp. 26S-38S.
Osborne C S et al, "Epidermal-Dermal Interactions Regulate Gelatinase Activity in APLIGRAF a Tissue-Engineered Human Skin Equivalent," British Journal of Dermatology, vol. 146(1) Jan. 2002, pp. 26-31.
Bello Y M et al, "Tissue-Engineered Skin Current Status in Wound Healing," American Journal of Clinical Dermatology, vol. 2(5) Jan. 1, 2001, pp. 305-313.
Vaalamo M et al, "Patterns of Matrix Metalloproteinase and TIMP-1 Expression in Chronic and Normally Healing Human Cutaneous Wounds," British Journal of Dermatology, vol. 135 (1) Jul. 1, 1996, pp. 52-59.
English Translation of Abstract: Japanese Publication No. 09-012478; Applicant: Fuji Yakuhin Kogyo KK; Published: Jan. 14, 1997 (Abstract Only) (1 Pg.).
Vogt, Peter M., et al., "Genetically modified keratinocytes transplanted to wounds reconstitute the epidermis," Proc Natl. Acad. Sci. USA, vol. 91, pp. 9307-9311 (1994).
Hayakawa, T., et al., "Growth-promoting activity of tissue inhibitor of metalloproteinases-1 (TIMP-1) for a wide range of cells a possible new growth factor in serum", FEBS Letters, vol. 298, Issue 1, Feb. 17, 1992, pp. 29-32 (Abstract and p. 952, col. 2).

* cited by examiner

*Primary Examiner* — Christopher M Babic
*Assistant Examiner* — Kelaginamane T Hiriyanna
(74) *Attorney, Agent, or Firm* — Casimir Jones, S.C.

(57) ABSTRACT

The present invention relates generally to compositions for wound healing. More specifically, the present invention provides human skin equivalents engineered to express exogenous proteinase inhibitor polypeptides (e.g., TIMP-1 polypeptides) and compositions and methods for making human skin equivalents engineered to express exogenous polypeptides. In addition, the present invention provides methods for treatment of wounds with human skin equivalents engineered to express exogenous polypeptides.

7 Claims, 15 Drawing Sheets

Figure 8

SEQ ID NO:1

```
1    aggggcctta gcgtgccgca tcgccgagat ccagcgccca gagagacacc agagaaccca
61   ccatggcccc ctttgagccc ctggcttctg gcatcctgtt gttgctgtgg ctgatagccc
121  ccagcagggc ctgcacctgt gtcccacccc acccacagac ggccttctgc aattccgacc
181  tcgtcatcag ggccaagttc gtggggacac cagaagtcaa ccagaccacc ttataccagc
241  gttatgagat caagatgacc aagatgtata aagggttcca agccttaggg gatgccgctg
301  acatccggtt cgtctacacc cccgccatgg agagtgtctg cggatacttc cacaggtccc
361  acaaccgcag cgaggagttt ctcattgctg gaaaactgca ggatggactc ttgcacatca
421  ctacctgcag tttcgtggct ccctggaaca gcctgagctt agctcagcgc cggggcttca
481  ccaagaccta cactgttggc tgtgaggaat gcacagtgtt ccctgtttta tccatcccct
541  gcaaactgca gagtggcact cattgcttgt ggacggacca gctcctccaa ggctctgaaa
601  agggcttcca gtcccgtcac cttgcctgcc tgcctcggga gccagggctg tgcacctggc
661  agtccctgcg gtcccagata gcctgaatcc tgcccggagt ggaactgaag cctgcacagt
721  gtccaccctg ttcccactcc catctttctt ccggacaatg aaataaagag ttaccaccca
781  gc
```

SEQ ID NO:2

MAPFEPLASGILLLLWLIAPSRACTCVPPHPQTAFCNSDLVIRAKFVGTPEVNQTTLYQRYEIKMTKMYKG
FQALGDAADIRFVYTPAMESVCGYFHRSHNRSEEFLIAGKLQDGLLHITTCSFVAPWNSLSLAQRRGFTKT
YTVGCEECTVFPCLSIPCKLQSGTHCLWTDQLLQGSEKGFQSRHLACLPREPGLCTWQSLRSQIA

Figure 9

SEQ ID NO:3

```
  1  cagagtcact cctgccttca ccatgaagtc cagcggcctc ttccccttcc tggtgctgct
 61  tgccctggga actctggcac cttgggctgt ggaaggctct ggaaagtcct tcaaagctgg
121  agtctgtcct cctaagaaat ctgcccagtg ccttagatac aagaaacctg agtgccagag
181  tgactggcag tgtccaggga agaagagatg ttgtcctgac acttgtggca tcaaatgcct
241  ggatcctgtt gacaccccaa acccaacaag gaggaagcct gggaagtgcc cagtgactta
301  tggccaatgt ttgatgctta accccccaa tttctgtgag atggatggcc agtgcaagcg
361  tgacttgaag tgttgcatgg gcatgtgtgg gaaatcctgc gtttcccctg tgaaagcttg
421  attcctgcca tatggaggag gctctggagt cctgctctgt gtggtccagg tcctttccac
481  cctgagactt ggctccacca ctgatatcct cctttgggga aaggcttggc acacagcagg
541  ctttcaagaa gtgccagttg atcaatgaat aaataaacga gcctatttct ctttgcac
```

SEQ ID NO:4

MKSSGLFPFLVLLALGTLAPWAVEGSGKSFKAGVCPPKKSAQCLRYKKPECQSDWQCPG
KKRCCPDTCGIKCLDPVDTPNPTRRKPGKCPVTYGQCLMLNPPNFCEMDGQCKRDLKCC
MGMCGKSCVSPVKA

HUMAN SKIN EQUIVALENTS EXPRESSING EXOGENOUS POLYPEPTIDES

This application claims priority to provisional patent application Ser. No. 60/657,592, filed Mar. 1, 2005, which is herein incorporated by reference in its entirety.

STATEMENT REGARDING FEDERALLY SPONSORED RESEARCH OR DEVELOPMENT

This invention was made with government support under STTR Grants R41-AG026714-01, 2R42AG026174-02, and R42-AG026714-02A1 awarded by the National Institutes of Health. The Government has certain rights in the invention.

FIELD OF THE INVENTION

The present invention relates generally to compositions for wound healing. More specifically, the present invention provides human skin equivalents engineered to express exogenous proteinase inhibitor polypeptides (e.g., tissue inhibitor of metalloproteinase-1 (TIMP-1)) and compositions and methods for making human skin equivalents engineered to express exogenous polypeptides. In addition, the present invention provides methods for treatment of wounds with human skin equivalents engineered to express exogenous polypeptides.

BACKGROUND

Chronic wounds affect three million people each year in the U.S. Chronic wounds generally involve any break, or ulceration, of the skin that is of long duration or recurs frequently. Chronic wounds disrupt the integrity of the skin by tearing, cutting, piercing or breaking the tissue. The causes may be structural, such as injury, or physiological, such as an underlying disease.

Chronic wounds occur in individuals with underlying diseases of various types whose medical conditions compromise the body's ability to repair injured tissue on its own. Despite the use of a variety of medical and surgical treatments, chronic wounds can take months or even years to heal and frequently recur. These wounds are often large and unsightly and may be painful in some patients.

Such wounds cause pain, loss of function, force changes in an individual's life through potential lack of mobility, require extended periods of time for recovery, and necessitate high amounts of patient compliance for recovery.

Chronic wounds are a serious health concern with substantial morbidity. They also are a source of frustration to both physician and patient, as lengthy treatments, treatment failures and the need for long periods of patient compliance prove challenging. The wounds take such a long time to heal, that compliance drops off and worsens when reversals occur or new ulcers appear.

Chronic wounds are of three major types: venous stasis ulcers, diabetic ulcers and pressure ulcers. A venous ulcer is an ulceration that develops on the ankle or lower leg in patients with chronic vascular disease. In these patients, blood flow in the lower extremities is impaired, leading to edema (swelling) and mild redness and scaling of the skin that gradually progress to ulceration. Venous ulcers are a condition affecting 500,000-700,000 patients in the US and 1.3 million people in the industrialized world.

A diabetic ulcer is a chronic wound that occurs in patients with diabetes. While the actual cause of the ulcer in these patients is an injury such as a callus, blister or foreign body such as a pebble or splinter, it is the patient's underlying disease that places him or her at high risk for developing an ulcer. Important risk factors include: inadequate local blood supply, which impairs their ability to repair injured tissue and ward off infection, and reduced sensation in the extremities, which causes the initial injury to go unrecognized until it becomes a serious, chronic wound. Diabetic ulcers are a condition affecting just under 500,000 patients in the US and 1.2 million people in the industrialized world.

A pressure ulcer is defined as any lesion caused by unrelieved pressure on tissues that are located over a bony prominence on the body. Pressure ulcers were formerly referred to as bedsores or decubitus ulcers. Pressure ulcers develop in immobile patients whose tissues are subjected to continuous pressure from bones on the interior and hard surfaces such as beds or chairs on the exterior. In addition to their immobility, patients at risk for the development of pressure ulcers typically have poor nutritional status, inadequate hydration, and other underlying medical conditions that compromise their ability to heal injuries. Pressure ulcers affect over 1.6 million people in the US and 4.1 million people in the industrialized world. Estimates of the prevalence of these conditions vary greatly. Estimates as high as 12 million patients have been reported for all types of chronic wounds in the industrialized markets.

Chronic wounds can be of variable sizes and depths. In general, there are four layers of tissue that can potentially sustain injury in a wound, the epidermis, or outermost layer; the dermis; the subcutaneous tissue; and, at the deepest layer, muscle, tendon, and bone. Partial-thickness ulcers involve a loss of skin that is limited to the epidermis and, potentially, part of the dermis. These wounds heal by epithelialization (proliferation and migration of epithelial cells). Full-thickness ulcers involve damage or necrosis of the epidermis, dermis, and subcutaneous tissue, and may extend into the connective tissue below the dermis. These wounds heal by granulation (filling of the wound with connective tissue), contraction, and epithelialization. The most severe category of ulcer involves injury to the epidermis, dermis, subcutaneous tissue, and muscle, tendon, or bone. The wound healing process is not complete even after the wound has closed. The process of rebuilding normal skin and tissue in a wound can take up to two years after the initial injury.

Treatment of chronic wounds varies with the severity of the wound. Partial- and full-thickness wounds are typically treated with dressings and debridement (use of chemicals or surgery to clear away necrotic, or dead, tissue). Antibiotics may be used in the event of an infection. Partial-thickness to full-thickness wounds represent the largest categories of chronic wound patients, the areas of greatest unmet medical need, and the categories most amenable to treatment with prescription growth factor therapy such as Repifermin. Patients with full-thickness wounds extending into muscle, tendon or bone are at significant risk of sepsis and are typically treated with surgery.

Despite the number of conservative therapies available, chronic wounds remain a very frustrating problem for health care practitioners because of the time-consuming nature of treatment regimens and patient non-compliance. What is needed is a therapy that can increase a practitioner's success in healing chronic wounds and/or accelerate the rate of chronic wound healing.

SUMMARY OF THE INVENTION

The present invention relates generally to compositions for wound healing. More specifically, the present invention provides human skin equivalents engineered to express exogenous proteinase inhibitor polypeptides (e.g., tissue inhibitor of metalloproteinase-1 (TIMP-1)) and compositions and methods for making human skin equivalents engineered to express exogenous polypeptides. In addition, the present invention provides methods for treatment of wounds with human skin equivalents engineered to express exogenous polypeptides.

Accordingly, in some embodiments, the present invention provides a method for providing cells expressing a heterologous proteinase inhibitor (e.g., a metalloproteinase inhibitor such as TIMP-1) comprising: providing a host cell (e.g., primary keratinocytes, keratinocyte precursors, immortalized keratinocytes, or transdifferentiated keratinocytes) and an expression vector comprising a DNA sequence encoding a proteinase inhibitor (e.g., TIMP-1) operably linked to a regulatory sequence; introducing the expression vector to the host cell; and culturing the host cell under conditions such that the proteinase inhibitor is expressed. In some embodiments, the host cell is capable of stratifying into squamous epithelia. In some embodiments, the method further comprises co-culturing the host cells with cells derived from a patient. In some embodiments, the immortalized keratinocytes are NIKS cells or cells derived from NIKS cells. In some embodiments, the expression vector further comprises a selectable marker. In certain embodiments, the regulatory sequence is a promoter sequence (e.g., a K14, ubiquitin or involucrin promoter or a portion thereof). In preferred embodiments, the promoter sequence allows proteinase inhibitor expression in the host cell. In preferred embodiments, the TIMP-1 is full length TIMP-1. The present invention further provides a host cell produced by the above described method.

The present invention additionally provides a composition comprising host cells expressing heterologous proteinase (e.g., TIMP-1) inhibitors, wherein the host cells are primary keratinocytes, keratinocyte precursors, immortalized keratinocytes, or transdifferentiated keratinocytes (e.g., NIKS cells or cells derived from NIKS cells). In some preferred embodiments, the TIMP-1 is full length TIMP-1. In some embodiments, the composition further comprises second host cells expressing a second heterologous polypeptide.

In yet other embodiments, the present invention provides a method of treating wounds comprising: providing a host cell (e.g., primary keratinocytes, keratinocyte precursors, transdifferentiated keratinocytes, or immortalized keratinocytes) (e.g., NIKS cells or cells derived from NIKS cells) expressing a heterologous proteinase inhibitor (e.g., TIMP-1), and a subject with a wound; and contacting the wound with the immortalized cells expressing the heterologous metalloproteinase inhibitor. In some embodiments, the contacting comprises topical application, engraftment or wound dressing. In some embodiments, the wounds are venous ulcers, diabetic ulcers, pressure ulcers, burns, ulcerative colitis, mucosal injuries, internal injuries, or external injuries. In certain embodiments, the host cells are incorporated into a human tissue (e.g., a human skin equivalent). In some embodiments, the human skin equivalent further comprises cells derived from a patient. In some embodiments, the method further comprises mixing the host cells expressing heterologous proteinase inhibitors (e.g., TIMP-1) with cells derived from the subject prior to the contacting step.

In still further embodiments, the present invention provides a vector comprising a keratinocyte specific promoter operably linked to a DNA sequence encoding a heterologous proteinase inhibitor (e.g., TIMP-1). In some embodiments, the keratinocyte specific promoter is the K14 promoter, ubiquitin or the involucrin promoter. In some embodiments, the vector further comprises a selectable marker. In some embodiments, the present invention provides a host cell comprising the vector. In other embodiments, the present invention further provides a human tissue (e.g., a skin equivalent) comprising the host cell. In some embodiments, the human skin equivalent further comprises cells derived from a patient.

DESCRIPTION OF THE FIGURES

FIG. 8 shows the nucleic acid (SEQ ID NO:1) and amino acid (SEQ ID NO:2) sequences of TIMP-1.

FIG. 9 shows the nucleic acid (SEQ ID NO:3) and amino acid (SEQ ID NO:4) sequence of SLPI.

DEFINITIONS

Figure 1:
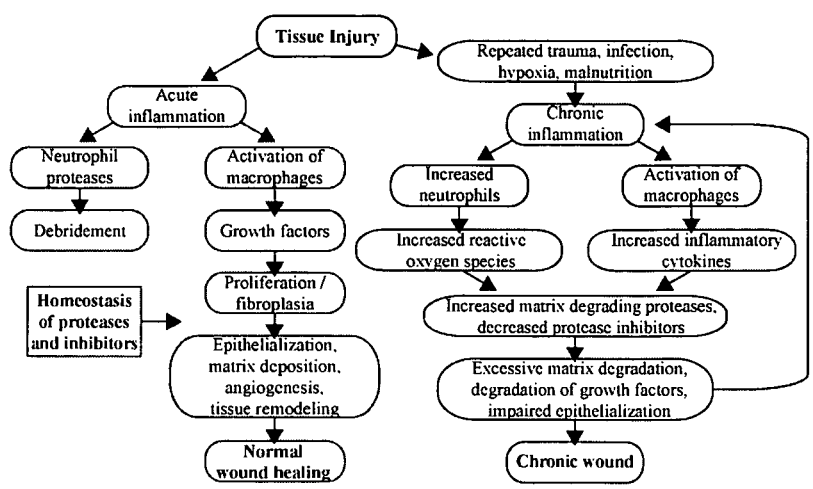
FIG. 1 shows a comparison of normal and chronic tissue repair responses.

As used herein, the term "growth factor" refers to extracellular molecules that bind to a cell-surface triggering an intracellular signaling pathway leading to proliferation, differentiation, or other cellular response. Examples of growth factors include, but are not limited to, growth factor I, trophic factor, $Ca^{2+}$, insulin, hormones, synthetic molecules, pharmaceutical agents, and LDL.

As used herein, the term "proteinase inhibitor" refers to a protein or other molecule that inhibits the activity of a proteinase (e.g., proteinase activity). In some embodiments, the proteinase is a metalloproteinase and the inhibitor is a metalloproteinase inhibitor (e.g., a tissue inhibitor of metalloproteinase or TIMP). In other embodiments, the proteinase is a serine proteinase (e.g., elastase) and the inhibitor is a serine proteinase inhibitor (e.g., SLPI).

As used herein, the terms "tissue inhibitor of metalloproteinase-1" or "TIMP-1", when used in reference to a protein or nucleic acid refers to a protein or nucleic acid encoding a protein that shares greater than about 50% identity with SEQ ID NO: 2 and also has at least one activity of wild type TIMP-1. Thus, the term TIMP-1 protein encompasses both proteins that are identical to wild-type TIMP-1 protein and those that are derived from wild type TIMP-1 protein (e.g., variants of TIMP-1 protein or chimeric genes constructed with portions of TIMP-1 protein coding regions).

As used herein, the term "activity of TIMP-1" refers to any activity of wild type TIMP-1 protein (e.g., inhibition of metalloproteinases). The term is intended to encompass all activities of TIMP-1 protein, alone or in combination.

In particular, the term "TIMP-1 gene" refers to the full-length TIMP-1 nucleotide sequence (e.g., contained in SEQ ID NO:1). However, it is also intended that the term encompass fragments of the TIMP-1 sequence, as well as other domains within the full-length TIMP-1 nucleotide sequence, as well as variants of TIMP-1. Furthermore, the terms "TIMP-1 gene nucleotide sequence" or "TIMP-1 gene polynucleotide sequence" encompasses DNA, cDNA, and RNA (e.g., mRNA) sequences.

As used herein, the term "NIKS cells" refers to cells having the characteristics of the cells deposited as cell line ATCC CRL-12191.

As used herein, the term "keratinocyte precursor" refers to any cell type that can differentiate into a keratinocyte (e.g., pluripotent or totipotent cell type).

As used herein, the term "transdifferentiated keratinocyte" refers to any cell or cell type that results from the transdifferentiation of a primary keratinocyte or an immortalized keratinocyte.

The term "gene" refers to a nucleic acid (e.g., DNA) sequence that comprises coding sequences necessary for the production of a polypeptide or precursor (e.g., GKLF). The polypeptide can be encoded by a full length coding sequence or by any portion of the coding sequence so long as the desired activity or functional properties (e.g., enzymatic activity, ligand binding, signal transduction, etc.) of the full-length or fragment are retained. The term also encompasses the coding region of a structural gene and the including sequences located adjacent to the coding region on both the 5' and 3' ends for a distance of about 1 kb on either end such that the gene corresponds to the length of the full-length mRNA. The sequences that are located 5' of the coding region and which are present on the mRNA are referred to as 5' untranslated sequences. The sequences that are located 3' or downstream of the coding region and that are present on the mRNA are referred to as 3' untranslated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

As used herein, the term "recombinant DNA molecule" as used herein refers to a DNA molecule that is comprised of segments of DNA joined together by means of molecular biological techniques.

The term "isolated" when used in relation to a nucleic acid, as in "an isolated oligonucleotide" or "isolated polynucleotide" refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids are nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding TIMP-1 includes, by way of example, such nucleic acid in cells ordinarily expressing TIMP-1 where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may be single-stranded), but may contain both the sense and anti-sense strands (i.e., the oligonucleotide or polynucleotide may be double-stranded).

As used herein the term "portion" when in reference to a nucleotide sequence (as in "a portion of a given nucleotide sequence") refers to fragments of that sequence. The fragments may range in size from four nucleotides to the entire nucleotide sequence minus one nucleotide (10 nucleotides, 20, 30, 40, 50, 100, 200, etc.).

As used herein the term "coding region" when used in reference to structural gene refers to the nucleotide sequences that encode the amino acids found in the nascent polypeptide as a result of translation of a mRNA molecule. The coding region is bounded, in eukaryotes, on the 5' side by the nucleotide triplet "ATG" that encodes the initiator methionine and on the 3' side by one of the three triplets that specify stop codons (i.e., TAA, TAG, TGA).

As used herein, the term "purified" or "to purify" refers to the removal of contaminants from a sample.

As used herein, the term "vector" is used in reference to nucleic acid molecules that transfer DNA segment(s) from one cell to another. The term "vehicle" is sometimes used interchangeably with "vector."

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

A "regulatory sequence" refers to a polynucleotide sequence that is necessary for regulation of expression of a coding sequence to which the polynucleotide sequence is operably linked. The nature of such regulatory sequences differs depending upon the host organism. In prokaryotes, such regulatory sequences generally include, for example, a promoter, and/or a transcription termination sequence. In eukaryotes, generally, such regulatory sequences include, for example, a promoter and/or a transcription termination sequence. The term "regulatory sequence" may also include additional components the presence of which are advantageous, for example, a secretory leader sequence for secretion of the polypeptide attached thereto.

"Operably linked" refers to a juxtaposition wherein the components so described are in a relationship permitting them to function in their intended manner. A regulatory sequence is "operably linked" to a coding sequence when it is joined in such a way that expression of the coding sequence is achieved under conditions compatible with the regulatory sequence.

"PCR" refers to the techniques of the polymerase chain reaction as described in Saiki, et al., Nature 324:163 (1986); and Scharf et al., Science 233:1076-1078 (1986); U.S. Pat. No. 4,683,195; and U.S. Pat. No. 4,683,202. As used herein, x is "heterologous" with respect to y if x is not naturally associated with y or x is not associated with y in the same manner as is found in nature.

"Pharmaceutically acceptable carrier," refers to any carrier that is used by persons in the art for administration into a human that does not itself induce any undesirable side effects such as the production of antibodies, fever, etc. Suitable carriers are typically large, slowly metabolized macromolecules that can be a protein, a polysaccharide, a polylactic acid, a polyglycolic acid, a polymeric amino acid, amino acid copolymers or an inactive virus particle. Such carriers are well known to those of ordinary skill in the art. Preferably the carrier is thyroglobulin.

As used herein, the term "host cell" refers to any eukaryotic or prokaryotic cell (e.g., bacterial cells such as $E.$ $coli$, yeast cells, mammalian cells, avian cells, amphibian cells, plant cells, fish cells, and insect cells), whether located in vitro or in vivo. For example, host cells may be located in a transgenic animal.

The terms "overexpression" and "overexpressing" and grammatical equivalents, are used in reference to levels of mRNA to indicate a level of expression higher (e.g., at least 2 fold and preferably at least 3 fold higher) than that typically observed in a given tissue in a control or non-transgenic animal. Levels of mRNA are measured using any of a number of techniques known to those skilled in the art including, but not limited to Northern blot or reverse transcription analysis. Appropriate controls are included on the Northern blot to control for differences in the amount of RNA loaded from each tissue analyzed (e.g., the amount of 28S rRNA, an abundant RNA transcript present at essentially the same amount in all tissues, present in each sample can be used as a means of normalizing or standardizing the TIMP-1 mRNA-specific signal observed on Northern blots). The amount of mRNA present in the band corresponding in size to the correctly spliced TIMP-1 transgene RNA is quantified; other minor species of RNA which hybridize to the transgene probe are not considered in the quantification of the expression of the transgenic mRNA.

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA does not integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

The term "calcium phosphate co-precipitation" refers to a technique for the introduction of nucleic acids into a cell. The uptake of nucleic acids by cells is enhanced when the nucleic acid is presented as a calcium phosphate-nucleic acid co-precipitate. The original technique of Graham and van der Eb (Graham and van der Eb, Virol., 52:456 [1973]) has been modified by several groups to optimize conditions for particular types of cells. The art is well aware of these numerous modifications.

The term "test compound" refers to any chemical entity, pharmaceutical, drug, and the like that can be used to treat or prevent a disease, illness, sickness, or disorder of bodily function, or otherwise alter the physiological or cellular status of a sample. Test compounds comprise both known and potential therapeutic compounds. A test compound can be determined to be therapeutic by screening using the screening methods of the present invention. A "known therapeutic compound" refers to a therapeutic compound that has been shown (e.g., through animal trials or prior experience with administration to humans) to be effective in such treatment or prevention.

The term "sample" as used herein is used in its broadest sense. A sample suspected of containing a human chromosome or sequences associated with a human chromosome may comprise a cell, chromosomes isolated from a cell (e.g., a spread of metaphase chromosomes), genomic DNA (in solution or bound to a solid support such as for Southern blot analysis), RNA (in solution or bound to a solid support such as for Northern blot analysis), cDNA (in solution or bound to a solid support) and the like. A sample suspected of containing a protein may comprise a cell, a portion of a tissue, an extract containing one or more proteins and the like.

As used herein, the term "response", when used in reference to an assay, refers to the generation of a detectable signal (e.g., accumulation of reporter protein, increase in ion concentration, accumulation of a detectable chemical product).

As used herein, the term "reporter gene" refers to a gene encoding a protein that may be assayed. Examples of reporter genes include, but are not limited to, luciferase (See, e.g., deWet et al., Mol. Cell. Biol. 7:725 [1987] and U.S. Pat. Nos. 6,074,859; 5,976,796; 5,674,713; and 5,618,682; all of which are incorporated herein by reference), green fluorescent protein (e.g., GenBank Accession Number U43284; a number of GFP variants are commercially available from CLONTECH Laboratories, Palo Alto, Calif.), chloramphenicol acetyltransferase, Beta-galactosidase, alkaline phosphatase, and horse radish peroxidase.

DETAILED DESCRIPTION

The present invention relates generally to compositions for wound healing. More specifically, the present invention provides human skin equivalents engineered to express exogenous proteinase inhibitor polypeptides (e.g., tissue inhibitor of metalloproteinase-1 (TIMP-1)) and compositions and methods for making human skin equivalents engineered to express exogenous polypeptides. In addition, the present invention provides methods for treatment of wounds with human skin equivalents engineered to express exogenous polypeptides.

I. Methods of Generating Host Cells

In some embodiments, the present invention provides methods of generating human tissues such as skin equivalents (e.g., from NIKS cells) expressing exogenous polypeptides (e.g., proteinase inhibitor polypeptides).

A) Host Cells

Generally, any source of cells or cell line that can stratify into squamous epithelia is useful in the present invention. Accordingly, the present invention is not limited to the use of any particular source of cells that are capable of differentiating into squamous epithelia. Indeed, the present invention contemplates the use of a variety of cell lines and sources that can differentiate into squamous epithelia, including both primary and immortalized keratinocytes. Sources of cells include keratinocytes and dermal fibroblasts biopsied from humans and cavaderic donors (Auger et al., In Vitro Cell. Dev. Biol.—Animal 36:96-103; U.S. Pat. Nos. 5,968,546 and 5,693,332, each of which is incorporated herein by reference), neonatal foreskins (Asbill et al., Pharm. Research 17(9): 1092-97 (2000); Meana et al., Burns 24:621-30 (1998); U.S. Pat. Nos. 4,485,096; 6,039,760; and 5,536,656, each of which is incorporated herein by reference), and immortalized keratinocytes cell lines such as NM1 cells (Baden, In Vitro Cell. Dev. Biol. 23(3):205-213 (1987)), HaCaT cells (Boucamp et al., J. cell. Boil. 106:761-771 (1988)); and NIKS cells (Cell line BC-1-Ep/SL; U.S. Pat. No. 5,989,837, incorporated herein by reference; ATCC CRL-12191). Each of these cell lines can be cultured or genetically modified as described below in order to produce a cell line capable of expressing an exogenous polypeptide.

In particularly preferred embodiments, NIKS cells or cells derived from NIKS cells are utilized. NIKS cells (Cell line BC-1-Ep/SL; U.S. Pat. Nos. 5,989,837, 6,514,711, 6,495,135, 6,485,724, and 6,214,567; each of which is incorporated herein by reference; ATCC CRL-12191). The discovery of a novel human keratinocyte cell line (near-diploid immortalized keratinocytes or NIKS) provides an opportunity to genetically engineer human keratinocytes for new therapeutic methods. A unique advantage of the NIKS cells is that they are a consistent source of genetically-uniform, pathogen-free human keratinocytes. For this reason, they are useful for the application of genetic engineering and genomic gene expression approaches to provide skin equivalent cultures with properties more similar to human skin. Such systems will provide an important alternative to the use of animals for testing compounds and formulations. The NIKS keratinocyte cell line, identified and characterized at the University of Wisconsin, is nontumorigenic, exhibits a stable karyotype, and undergoes normal differentiation both in monolayer and organotypic culture. NIKS cells form fully stratified skin equivalents in culture. These cultures are indistinguishable by all criteria tested thus far from organotypic cultures formed from primary human keratinocytes. Unlike primary cells however, the immortalized NIKS cells will continue to proliferate in monolayer culture indefinitely. This provides an opportunity to genetically manipulate the cells and isolate new clones of cells with new useful properties (Allen-Hoffmann et al., J. Invest. Dermatol., 114(3): 444-455 (2000)).

The NIKS cells arose from the BC-1-Ep strain of human neonatal foreskin keratinocytes isolated from an apparently normal male infant. In early passages, the BC-1-Ep cells exhibited no morphological or growth characteristics that were atypical for cultured normal human keratinocytes. Cultivated BC-1-Ep cells exhibited stratification as well as features of programmed cell death. To determine replicative lifespan, the BC-1-Ep cells were serially cultivated to senescence in standard keratinocyte growth medium at a density of $3 \times 10^5$ cells per 100-mm dish and passaged at weekly intervals (approximately a 1:25 split). By passage 15, most keratinocytes in the population appeared senescent as judged by the presence of numerous abortive colonies that exhibited large, flat cells. However, at passage 16, keratinocytes exhibiting a small cell size were evident. By passage 17, only the small-sized keratinocytes were present in the culture and no large, senescent keratinocytes were evident. The resulting population of small keratinocytes that survived this putative crisis period appeared morphologically uniform and produced colonies of keratinocytes exhibiting typical keratinocyte characteristics including cell-cell adhesion and apparent squame production. The keratinocytes that survived senescence were serially cultivated at a density of $3 \times 10^5$ cells per 100-mm dish. Typically the cultures reached a cell density of approximately $8 \times 10^6$ cells within 7 days. This stable rate of cell growth was maintained through at least 59 passages, demonstrating that the cells had achieved immortality. The keratinocytes that emerged from the original senescent population were originally designated BC-1-Ep/Spontaneous Line and are now termed NIKS. The NIKS cell line has been screened for the presence of proviral DNA sequences for HIV-1, HIV-2, EBV, CMV, HTLV-1, HTLV-2, HBV, HCV, B-19 parvovirus, HPV-16 and HPV-31 using either PCR or Southern analysis. None of these viruses were detected.

Chromosomal analysis was performed on the parental BC-1-Ep cells at passage 3 and NIKS cells at passages 31 and 54. The parental BC-1-Ep cells have a normal chromosomal complement of 46, XY. At passage 31, all NIKS cells contained 47 chromosomes with an extra isochromosome of the long arm of chromosome 8. No other gross chromosomal abnormalities or marker chromosomes were detected. At passage 54, all cells contained the isochromosome 8.

The DNA fingerprints for the NIKS cell line and the BC-1-Ep keratinocytes are identical at all twelve loci analyzed demonstrating that the NIKS cells arose from the parental BC-1-Ep population. The odds of the NIKS cell line having the parental BC-1-Ep DNA fingerprint by random chance is $4 \times 10^{-16}$. The DNA fingerprints from three different sources of human keratinocytes, ED-1-Ep, SCC4 and SCC13y are different from the BC-1-Ep pattern. This data also shows that keratinocytes isolated from other humans, ED-1-Ep, SCC4, and SCC13y, are unrelated to the BC-1-Ep cells or each other. The NIKS DNA fingerprint data provides an unequivocal way to identify the NIKS cell line.

Loss of p53 function is associated with an enhanced proliferative potential and increased frequency of immortality in cultured cells. The sequence of p53 in the NIKS cells is identical to published p53 sequences (GenBank accession number: M14695). In humans, p53 exists in two predominant polymorphic forms distinguished by the amino acid at codon 72. Both alleles of p53 in the NIKS cells are wild-type and have the sequence CGC at codon 72, which codes for an arginine. The other common form of p53 has a proline at this position. The entire sequence of p53 in the NIKS cells is identical to the BC-1-Ep progenitor cells. Rb was also found to be wild-type in NIKS cells.

Anchorage-independent growth is highly correlated to tumorigenicity in vivo. For this reason, the anchorage-independent growth characteristics of NIKS cells in agar or methylcellulose-containing medium was investigated. After 4 weeks in either agar- or methylcellulose-containing medium, NIKS cells remained as single cells. The assays were continued for a total of 8 weeks to detect slow growing variants of the NIKS cells. None were observed.

To determine the tumorigenicity of the parental BC-1-Ep keratinocytes and the immortal NIKS keratinocyte cell line, cells were injected into the flanks of athymic nude mice. The human squamous cell carcinoma cell line, SCC4, was used as a positive control for tumor production in these animals. The injection of samples was designed such that animals received SCC4 cells in one flank and either the parental BC-1-Ep keratinocytes or the NIKS cells in the opposite flank. This injection strategy eliminated animal to animal variation in tumor production and confirmed that the mice would support vigorous growth of tumorigenic cells. Neither the parental BC-1-Ep keratinocytes (passage 6) nor the NIKS keratinocytes (passage 35) produced tumors in athymic nude mice.

NIKS cells were analyzed for the ability to undergo differentiation in both surface culture and organotypic culture. For cells in surface culture, a marker of squamous differentiation, the formation cornified envelopes was monitored. In cultured human keratinocytes, early stages of cornified envelope assembly result in the formation of an immature structure composed of involucrin, cystatin-α and other proteins, which represent the innermost third of the mature cornified envelope. Less than 2% of the keratinocytes from the adherent BC-1-Ep cells or the NIKS cell line produce cornified envelopes. This finding is consistent with previous studies demonstrating that actively growing, subconfluent keratinocytes produce less than 5% cornified envelopes. To determine whether the NIKS cell line is capable of producing cornified envelopes when induced to differentiate, the cells were removed from surface culture and suspended for 24 hours in medium made semi-solid with methylcellulose. Many aspects of terminal differentiation, including differential expression of keratins and cornified envelope formation can be triggered in vitro by loss of keratinocyte cell-cell and cell-substratum adhesion. The NIKS keratinocytes produced as many as and usually more cornified envelopes than the parental keratinocytes. These findings demonstrate that the NIKS keratinocytes are not defective in their ability to initiate the formation of this cell type-specific differentiation structure.

To confirm that the NIKS keratinocytes can undergo squamous differentiation, the cells were cultivated in organotypic culture. Keratinocyte cultures grown on plastic substrata and submerged in medium replicate but exhibit limited differentiation. Specifically, human keratinocytes become confluent and undergo limited stratification producing a sheet consisting of 3 or more layers of keratinocytes. By light and electron microscopy there are striking differences between the architecture of the multilayered sheets formed in tissue culture and intact human skin. In contrast, organotypic culturing techniques allow for keratinocyte growth and differentiation under in vivo-like conditions. Specifically, the cells adhere to a physiological substratum consisting of dermal fibroblasts embedded within a fibrillar collagen base. The organotypic culture is maintained at the air-medium interface. In this way, cells in the upper sheets are air-exposed while the proliferating basal cells remain closest to the gradient of nutrients provided by diffusion through the collagen gel. Under these conditions, correct tissue architecture is formed. Several characteristics of a normal differentiating epidermis are evident. In both the parental cells and the NIKS cell line a single layer of cuboidal basal cells rests at the junction of the epidermis and the dermal equivalent. The rounded morphology and high nuclear to cytoplasmic ratio is indicative of an actively dividing population of keratinocytes. In normal human epidermis, as the basal cells divide they give rise to daughter cells that migrate upwards into the differentiating layers of the tissue. The daughter cells increase in size and become flattened and squamous. Eventually these cells enucleate and form cornified, keratinized structures. This normal differentiation process is evident in the upper layers of both the parental cells and the NIKS cells. The appearance of flattened squamous cells is evident in the upper layers of keratinocytes and demonstrates that stratification has occurred in the organotypic cultures. In the uppermost part of the organotypic cultures the enucleated squames peel off the top of the culture. To date, no histological differences in differentiation at the light microscope level between the parental keratinocytes and the NIKS keratinocyte cell line grown in organotypic culture have been observed.

To observe more detailed characteristics of the parental (passage 5) and NIKS (passage 38) organotypic cultures and to confirm the histological observations, samples were analyzed using electron microscopy. Parental cells and the immortalized human keratinocyte cell line, NIKS, were harvested after 15 days in organotypic culture and sectioned perpendicular to the basal layer to show the extent of stratification. Both the parental cells and the NIKS cell line undergo extensive stratification in organotypic culture and form structures that are characteristic of normal human epidermis. Abundant desmosomes are formed in organotypic cultures of parental cells and the NIKS cell line. The formation of a basal lamina and associated hemidesmosomes in the basal keratinocyte layers of both the parental cells and the cell line was also noted.

Hemidesmosomes are specialized structures that increase adhesion of the keratinocytes to the basal lamina and help maintain the integrity and strength of the tissue. The presence of these structures was especially evident in areas where the parental cells or the NIKS cells had attached directly to the porous support. These findings are consistent with earlier ultrastructural findings using human foreskin keratinocytes cultured on a fibroblast-containing porous support. Analysis at both the light and electron microscopic levels demonstrate that the NIKS cell line in organotypic culture can stratify, differentiate, and form structures such as desmosomes, basal lamina, and hemidesmosomes found in normal human epidermis.

B) Proteinase Inhibitors

In some embodiments, the present invention provides human skin equivalents expressing exogenous or heterologous proteinases inhibitors. The present invention is not limited to a particular proteinases inhibitor. Exemplary proteinases inhibitors are described herein.

i) Metalloproteinase inhibitors

In some embodiments, the proteinases inhibitors are metalloproteinase inhibitors. For example, in some embodiments, the present invention provides human skin equivalents (e.g., keratinocytes) that express exogenous or heterologous TIMP-1. Human skin is composed of a vascularized dermal layer containing fibroblasts embedded in an extracellular matrix and an epidermal layer consisting primarily of keratinocytes that differentiate to form the outermost, impermeable skin layer. Differentiated keratinocytes are continuously lost from the surface and replaced by the proliferation of basal keratinocytes. The rate at which a basal cell initiates and completes its differentiation program is tightly regulated, although the molecular controls for such regulation are ill defined [Fuchs, J. Cell. Sci. Suppl., 1993. 17: p. 197-208]. In vivo, the stages of the terminal differentiation process are characterized by numerous changes including filaggrin-mediated keratin intermediate filament bundling, and release of lipids from membrane-coating granules into the intercellular space [Schurer et al., Dermatologica, 1991. 183: p. 77-94]. The cornified envelope, another terminal differentiation structure consisting of several proteins covalently cross-linked by the action of calcium-dependent transglutaminases, is also formed in differentiating keratinocytes [Reichert et al., The cornified envelope: a key structure of terminally differentiating keratinocytes, in Molecular Biology of the Skin, M. Darmon, Editor. 1993, Academic Press, Inc.: San Diego. p. 107-150; Aeschlimann et al., Thrombosis & Haemostasis, 1994. 71(4): p. 402-15]. Ultimately keratinocytes lose intracellular organelles and enucleate in the stratum corneum, forming a shell with high tensile strength.

Numerous molecular differences are associated with intrinsic cutaneous aging [Gosain and DiPietro, World J Surg, 2004. 28(3): p. 321-6]. Keratinocytes migrate from the basal layer to the outermost skin layer at a rate 50% faster than in younger individuals. In addition, there is a flattening of the dermal-epidermal junction, which predisposes aged skin to separation. Moreover, fewer keratinocytes and fibroblasts are present in aged skin. Elastin morphology in the dermis is abnormal which may result in less elasticity. Collagen production is decreased and degradation is increased. An increase in MMP activity resulting from upregulation of MMPs and down-regulation of TIMPs, is responsible for the lysis of elastin fibers and dermal collagen during skin aging. Specifically, TIMP-1 and -2 mRNA levels were found to be significantly lower in aged skin when compared to young skin aging [Hornebeck, Pathol Biol (Paris), 2003. 51(10): p. 569-73; Ashcroft et al., J Pathol, 1997. 183(2): p. 169-76]. The authors concluded that the elderly are predisposed to chronic wound states due to dermal tissue breakdown and retarded wound healing resulting from a decrease in TIMP levels.

Cutaneous wound healing involves a complex interaction between epidermal and dermal cells, the extracellular matrix, plasma-derived proteins, and controlled angiogenesis coordinated by an array of cytokines and growth factors. This dynamic process is classically divided into three overlapping phases: inflammation, proliferation, and remodeling of the extracellular matrix (reviewed in [Martin, Science, 1997. 276 (5309): p. 75-81; Diegelmann and Evans, Front Biosci, 2004. 9: p. 283-9.]).

Upon injury, growth factors initiate the wound closure response by providing chemotactic cues to recruit circulating inflammatory cells (primarily neutrophils) to the wound site. Proteases are released during the acute inflammatory phase and assist with the removal of damaged and denatured extracellular matrix components (debridement) in preparation for the subsequent proliferative phase. As the epidermal cells proliferate and migrate forward to re-epithelialize the denuded wound surface, fibroblasts produce new extracellular matrix in the form of contractile granulation tissue that draws the wound margins together. Once the denuded wound surface has been covered by a monolayer of keratinocytes, epidermal migration ceases and a new stratified epidermis with underlaying basement membrane is reestablished from the margins of the wound inward. Collagen production within the dermal compartment continues for several weeks after wound closure and subsequent extracellular matrix remodeling may continue for two years or more.

Many local and systemic factors contribute to impaired healing. As described above, normal cutaneous healing proceeds in an ordered, highly regulated manner. In a chronic wound environment these complex cellular and molecular processes are disrupted and incorrectly regulated resulting in a failure to form granulation tissue and to re-epithelialize. Some features common to chronic wounds include elevated levels of proinflammatory cytokines, diminished growth factor activity, and the inability of cells to respond correctly to molecular regulators (FIG. 1) [Agren et al., J Invest Dermatol, 1999. 112(4): p. 463-9; Mendez et al., J Vasc Surg, 1999. 30(4): p. 734-43; Mendez et al., J Vasc Surg, 1998. 28(6): p. 1040-50]. These cellular and biochemical differences have been termed cellular dysfunction and biochemical imbalance [Enoch and Harding, Wounds, 2003. 15(7): p. 213-229]. While these factors all contribute to the persistent chronic wound state, an abnormally high level of proteinase activity is a critical deviation from the typical sequence of repair [Mulder and Vande Berg, J Am Podiatr Med Assoc, 2002. 92(1): p. 34-7]. The present invention is not limited to a particular mechanism. Indeed, an understanding of the mechanism is not necessary to practice the present invention. Nonetheless, it is postulated that a persistent proinflammatory response, with ongoing recruitment and activation of inflammatory cells, leads to the release of large quantities of proteolytic enzymes overwhelming the local inhibitor defense [Barrick et al., Wound Repair Regen, 1999. 7(6): p. 410-22]. The resulting biochemical imbalance between proteinases and their inhibitors may lead to abnormal degradation of the extracellular matrix, degradation of critical soluble or matrix-associated growth factors, and breakdown of their respective cellular receptors within the wound environment further contributing to cellular dysfunction.

Cell migration, granulation tissue formation, neoangiogenesis, and extracellular matrix remodeling all require controlled degradation of the surrounding matrix mediated in large part by MMPs [Armstrong and Jude, J Am Podiatr Med Assoc, 2002. 92(1): p. 12-8]. MMPs are a family of enzymes sharing several characteristics: secretion as inactive zymogens; presence of a zinc ion at the catalytic site; specificity to degrade at least one component of the extracellular matrix; and inhibition by TIMPs. MMP family members are regulated at the level of gene transcription and by the controlled conversion of proenzymes to the active enzyme forms, as well as by the inhibitory activity of TIMPs [Nagase and Woessner J Biol Chem, 1999. 274(31): p. 21491-4; Visse and Nagase, Circ Res, 2003. 92(8): p. 827-39]. Four distinct subsets of enzymes exist within the MMP family: collagenases, gelatinases, stromelysins, and membrane-type metalloproteinases (MT-MMPs). The collagenases (MMP-1, -8, and -13) are the only mammalian enzymes with the capacity to cleave the triple helix of fibrillar collagen (types I, II, and III). The gelatinases (MMP-2 and -9) further degrade these denatured collagens, as well as other collagen types (IV, V, VII, and X), elastin, and basement membrane components. The stromelysins (MMP-3, -10, -11, and -12) play varied roles in degradation of the extracellular matrix. As suggested by their name, the membrane-associated MT-MMPs (MMP-14) are not secreted into the extracellular space. The MT-MMPs function by activating other MMPs and localizing their activity within a tissue microenvironment.

Recent years have seen major advances in knowledge of the diversity, biological roles, structures, and modes of action of TIMPs. TIMPs are integral to maintaining controlled degradation of the extracellular matrix during healing. The TIMP family is comprised of at least four distinct members, which possess 12 conserved cysteine residues and exhibit MMP inhibitory activity (reviewed in [Gomez et al., Eur J Cell Biol, 1997. 74(2): p. 111-22; Brew and Nagase, Biochim Biophys Acta, 2000. 1477(1-2): p. 267-83]). TIMPs are relatively small, two-domain molecules with each domain stabilized by three disulfide bonds. TIMPs bind to the zinc-binding site of active MMPs forming 1:1 enzyme-inhibitor complexes. As well as inhibiting activated MMPs, TIMPs may also bind the inactive proMMP zymogens thereby slowing the process of activation. Independent of MMP-inhibitory activity, other biological activities attributed to TIMPs include cell growth promotion, matrix binding, inhibition of angiogenesis, and induction of apoptosis [Baker et al., J Cell Sci, 2002. 115(Pt 19): p. 3719-27]. TIMPs have not been shown to be dominantly acting proto-oncogenes or tumor suppressor genes, and studies examining TIMP activities in tumorigenesis have been inconclusive [Jiang et al., Oncogene, 2002. 21(14): p. 2245-52; Rhee et al., Cancer Res, 2004. 64(3): p. 952-61].

Accordingly, in some embodiments, the present invention provides skin substitutes comprising exogenous TIMP-1 genes. Although TIMP-1 preferentially inhibits MMP-1, it is capable of inhibiting the activity of all known MMPs and as such plays a key role in maintaining the balance between extracellular matrix deposition and degradation [Gomez et al., Eur J Cell Biol, 1997. 74(2): p. 111-22]. A reduction in TIMP-1 levels has been shown to impact on the formation and perpetuation of chronic wound states. Moreover, several reports have demonstrated the growth promoting activities of TIMP-1 on a variety of cultured cells including, significantly, human keratinocytes [Hayakawa et al., FEBS Lett, 1992. 298(1): p. 29-32].

TIMP-1 is an extensively glycosylated protein produced and secreted by a variety of cell types including keratinocytes, fibroblasts, smooth muscle cells, and endothelial cells. TIMP-1 is encoded by a single gene approximately 3 kb in length, interrupted by at least two intervening sequences [Hayakawa et al., supra]. The human TIMP-1 mRNA encodes a protein of 207 amino acids. A signal peptide of 23 amino acids is cleaved to result in the final 184 amino acid protein with a relative molecular mass of approximately 29 kD [Docherty et al., Nature, 1985. 318(6041): p. 66-9].

TIMP-1 was shown to be identical to a factor identified previously as Erythroid Potentiating Activity which stimulates the growth of erythroid precursors [Gasson et al., Nature, 1985. 315(6022): p. 768-71]. Bertaux et al. found that recombinant TIMP-1 at 1-10 µg/ml stimulated growth of keratinocytes in monolayer culture while growth in three-dimensional organotypic culture was stimulated at 5-10 µg/ml [Bertaux et al., J Invest Dermatol, 1991. 97(4): p. 679-85]. However, Pilcher et al. found that very high levels of recombinant TIMP-1 (50 µg/ml) inhibited growth of primary keratinocytes on collagen type I [Pilcher et al., J Cell Biol, 1997. 137(6): p. 1445-57]. Recently Salonurmi et al. have reported that overexpression of TIMP-1 under the MMP-9 promoter delayed wound healing in a transgenic mouse model, presumably from affecting TIMP-1-mediated keratinocyte migration [Salonurmi et al., Cell Tissue Res, 2003]. It is contemplated that, without limiting the invention to a particular mechanism (the understanding of which is not necessary to practice the present invention), this result is to be expected in a normal wound healing environment, however, the highly proteolytic chronic wound state may require overexpression of TIMP-1 to balance excessive MMP activity.

Figure 2:
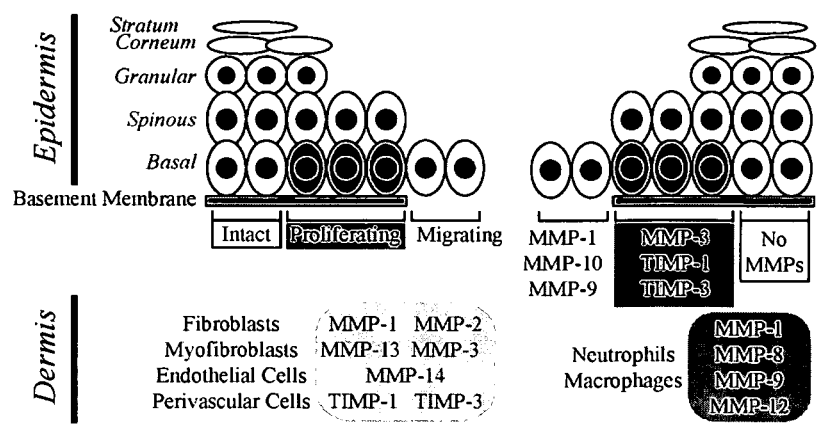
FIG. 2 shows induction of MMP and TIMP expression during normal wound healing.

MMP and TIMPs are induced in response to endogenous signals generated during wound healing such as cytokines, growth factors, altered cell-matrix interactions and altered cell-to-cell contacts. During normal wound healing, MMP and TIMP mRNA expression are spatially compartmentalized (FIG. 2). MMP and TIMP expression coincide temporally with the well-characterized inflammatory and proliferation phases of repair, in contrast to chronic wounds (Table 1) [Trengove et al., Wound Repair Regen, 1999. 7(6): p. 442-52; Vaalamo et al., Hum Pathol, 1999. 30(7): p. 795-802; Vaalamo et al., J Invest Dermatol, 1997. 109(1): p. 96-101; Soo et al., Plast Reconstr Surg, 2000. 105(2): p. 638-47]. In acute wounds TIMPs act to block tissue destruction by MMPs as the inflammatory phase terminates and repair proceeds into the proliferative phase. In chronic wounds, however, notable decreases in TIMP levels and sizable increases in MMP levels have been reported (see Table 2). Further evidence was provided by Ladwig et al. who found that the ratio of MMP-9/TIMP-1 in wound fluid from pressure ulcers served as a prognostic indicator of the outcome of healing [Ladwig et al., Wound Repair Regen, 2002. 10(1): p. 26-37]. This biochemical imbalance between proteinase activity and inhibition contributes to the establishment and perpetuation of a chronic wound environment [Bullen et al., J Invest Dermatol, 1995. 104(2): p. 236-40; Saito et al. J Vasc Surg, 2001. 34(5): p. 930-8; Ladwig et al., Wound Repair Regen, 2002. 10(1): p. 26-37; Soo et al., Plast Reconstr Surg, 2000. 105(2): p. 638-47; Weckroth et al., J Invest Dermatol, 1996. 106(5): p. 1119-24].

TABLE 1

Temporal mRNA expression of MMPs and TIMPs in normally healing cutaneous wounds and chronic ulcers.

| | Normally healing wounds | | | | | | Chronic ulcers | |
|---|---|---|---|---|---|---|---|---|
| | 1-2 days | | 3-5 days | | 6-11 days | | | |
| | E | D | E | D | E | D | E | D |
| Collagenase-1 (MMP-1) | + | + | + | + | − | + | + | + |
| Collagenase-3 (MMP-13) | − | − | − | − | − | − | − | + |
| Stryomelysin-1 (MMP-3) | + | + | + | + | − | + | + | + |
| Stromelysin-2 (MMP-10) | − | − | + | − | − | − | + | − |
| Metalloelastase (MMP-12) | − | − | − | − | − | − | − | + |
| TIMP-1 | − | + | + | + | − | + | − | + |
| TIMP-3 | − | + | + | + | − | + | − | + |

Epidermal (E) and dermal (D) compartments expression displayed separately.

TABLE 2

MMP and TIMP activities. Comparison of chronic wound fluid to acute wound (surgical and traumatic) fluid.

| Wound Type | MMP | | TIMP | |
|---|---|---|---|---|
| Mixed vessel disease ulcers, Pressure ulcers, and Diabetic foot ulcers Trengove et al. [5] | total MMP activity | 30-fold ↑ | TIMP-1 | 55-fold ↓ |
| Pressure ulcers Yager et al. [7] | MMP-2 MMP-9 | 10-fold ↑ 25-fold ↑ | NS | NS |
| Diabetic foot ulcers Lobmann et al. [9] | MMP-1 MMP-2 MMP-8 MMP-9 | 65-fold ↑ 6-fold ↑ 2-fold ↑ 14-fold ↑ | TIMP-2 | 2-fold ↓ |
| Venous stasis Bullen, et al. [10] | MMP-2 MMP-9 | Activity ↑ | TIMP-1 | 2.5-fold ↓ |

(NS-Not studied)

To date several broad-spectrum MMP inhibitors have been developed for the treatment of arthritis, cancer, periodontal disease, and corneal ulceration [Gomez et al., Eur J Cell Biol, 1997. 74(2): p. 111-22; Nagase and Brew, Arthritis Res, 2002. 4 Suppl 3: p. S51-61; Herouy et al., Eur J Dermatol, 2000. 10(3): p. 173-80; Catterall and Cawston, Arthritis Research and Therapy, 2002. 5(1): p. 12-24]. These synthetic small-molecule MMP inhibitors have had limited success in clinical trials with undesirable side effects [Jiang et al., Oncogene, 2002. 21(14): p. 2245-52]. For example, in cancer trials the MMP inhibitor MARIMASTAT caused musculoskeletal problems manifested by tendonitis, joint pain, stiffness and reduced mobility [Steward and Thomas, Expert Opin Investig Drugs, 2000. 9(12): p. 2913-22]. When Ilomastat and BB-3103 were tested specifically for the treatment of chronic wounds, the inhibitors abolished almost all MMP activity severely impairing epidermal regeneration [Agren et al., Exp Dermatol, 2001. 10(5): p. 337-48; Mirastschijski et al., J Invest Dermatol, 2002. 118(1): p. 55-64]. Commercially available PROMOGRAN, an oxidized regenerated cellulose/collagen matrix that binds MMPs in the wound site, has shown only marginal success in the treatment of diabetic foot ulcers when compared to moistened gauze [Veves et al., Arch Surg, 2002. 137(7): p. 822-7]. The most promising clinical results were demonstrated using the MMP inhibitor doxycycline. In this study, topical treatment of diabetic ulcers with doxycycline resulted in improved healing when compared to vehicle control [Chin et al., Wounds, 2003. 15(10): p. 315-323]. However, the small study size (7 patients) precluded drawing definitive conclusions. Although the approaches described above focus on the problem of excessive extracellular matrix degradation, the natural MMP inhibitor, TIMP-1, has not yet been explored as a chronic wound treatment.

In some embodiments, the present invention provides a skin substitute genetically-engineered to overexpress TIMP-1 protein. It is contemplated that this skin substitute will attenuate the highly proteolytic environment of the chronic wound in aged individuals. Not only will this product secrete endogenous factors and provide a physical and biological barrier against wound infection, it will act to restore the balance between proteinases and their inhibitors. Recently published studies by Terasaki and coworkers support this prediction. In these studies, not only did the application of recombinant TIMP-2 enhance in vitro keratinocyte migration, but faster wound closure was observed compared to vehicle-treated controls when recombinant TIMP-2 was applied to full-thickness wounds using several rodent models [Terasaki et al., J Dermatol, 2003. 30(3): p. 165-72]. Overexpression of TIMP-1 in a rat model of aneurysm demonstrated that MMP upregulation in this model results in structural destabilization of the blood vessel, leading to rupture. Allaire demonstrated that local overexpression of TIMP-1 decreased MMP-9, MMP-2, and elastase activity, thus greatly improving the structural integrity of the vessel tissue [Allaire et al., J Clin Invest, 1998. 102(7): p. 1413-20]. Numerous published reports have also demonstrated successful overexpression of TIMP-1 in mammalian cell lines [Allaire et al., supra; Li et al., Cancer Res, 1999. 59(24): p. 6267-75; Khokha, J Natl Cancer Inst, 1994. 86(4): p. 299-304; Roeb et al., J Cell Biochem, 1999. 75(2): p. 346-55] and transgenic mice [Kruger et al., Blood, 1997. 90(5): p. 1993-2000; Martin et al., Oncogene, 1996. 13(3): p. 569-76; Yoshiji et al., Hepatology, 2000. 32(6): p. 1248-54; Alexander et al., J Cell Biol, 1996. 135(6 Pt 1): p. 1669-77] using a variety of promoter strategies. The ability of TIMP-1 to both inhibit all members of the MMP family and promote the growth of keratinocytes make TIMP-1 well suited for the development of skin substitutes that inhibit the excessive proteolytic activity associated with chronic wounds.

ii) Other Proteinase Inhibitors

The present invention is not limited to the use of metalloproteinase inhibitors or TIMP-1. The present invention contemplates the use of any number of proteinase inhibitors to aid in wound healing. For example, in some embodiments, inhibitors of serine proteinases (e.g., elastase) inhibitors are utilized. In some embodiments, secretory leukocyte protease inhibitor (SLPI; SEQ ID NO:3) is utilized (See e.g., Lai et al., Wound Repair Regen. November-December 2004; 12(6):613-7).

C) Methods of Generating Host Cells Expressing Exogenous Polypeptides

In some embodiments, the present invention provides methods of generating host cells (e.g., keratinocytes) and skin equivalents expressing one or more exogenous proteinase inhibitor polypeptides (e.g., TIMP-1). The present invention is not limited to particular methods for the generation of such cells and skin equivalents. Exemplary methods are described below. Additional methods are known to those skilled in the relevant arts.

In certain embodiments, the proteinase inhibitor polypeptide cDNA is cloned into a cloning vector. A regulatory sequence that can be linked to the proteinase inhibitor polypeptide DNA sequence in an expression vector is a promoter that is operable in the host cell in which the proteinase inhibitor polypeptide is to be expressed. Optionally, other regulatory sequences can be used herein, such as one or more of an enhancer sequence, an intron with functional splice donor and acceptance sites, a signal sequence for directing secretion of the proteinase inhibitor, a polyadenylation sequence, other transcription terminator sequences, and a sequence homologous to the host cell genome. Other sequences, such as origin of replication, can be added to the vector as well to optimize expression of the desired proteinase inhibitor. Further, a selectable marker can be present in the expression vector for selection of the presence thereof in the transformed host cells.

In preferred embodiments, TIMP polypeptides are fused to a regulatory sequence that drives the expression of the polypeptide (e.g., a promoter). In preferred embodiments, the regulatory sequence is the involucrin promoter or the keratin-14 promoter. However, any promoter that directs expression of the proteinase inhibitor polypeptide in a desired host can be used in the present invention. Mammalian promoter sequences that can be used herein are those from mammalian viruses that are highly expressed and that have a broad host range. Examples include the SV40 early promoter, the Cytomegalovirus ("CMV") immediate early promoter mouse mammary tumor virus long terminal repeat ("LTR") promoter, adenovirus major late promoter (Ad MLP), and Herpes Simplex Virus ("HSV") promoter. In addition, promoter sequences derived from non-viral genes, such as the murine metallothionein gene, ubiquitin and elongation factor alpha (EF-1α) are also useful herein. These promoters can further be either constitutive or regulated, such as those that can be induced with glucocorticoids in hormone-responsive cells.

In some preferred embodiments, host cells (e.g., keratinocytes) expressing proteinase inhibitor polypeptides can be produced by conventional gene expression technology, as discussed in more detail below. The practice of the present invention will employ, unless otherwise indicated, conventional techniques of molecular biology, microbiology, recombinant DNA, and immunology, which are within the skill of the art. Such techniques are explained fully in the literature, including Sambrook, et al., MOLECULAR CLONING: A LABORATORY MANUAL 2nd ed. (Cold Spring Harbor Laboratory Press, 1989); DNA CLONING, Vol. I and II, D. N Glover ed. (IRL Press, 1985); OLIGONUCLEOTIDE SYNTHESIS, M. J. Gait ed. (IRL Press, 1984); NUCLEIC ACID HYBRIDIZATION, B. D. Hames & S. J. Higgins eds. (IRL Press, 1984); TRANSCRIPTION AND TRANSLATION, B. D. Hames & S. J. Higgins eds., (IRL Press, 1984); ANIMAL CELL CULTURE, R. I. Freshney ed. (IRL Press, 1986); IMMOBILIZED CELLS AND ENZYMES, K. Mosbach (IRL Press, 1986); B. Perbal, A PRACTICAL GUIDE TO MOLECULAR CLONING, Wiley (1984); the series, METHODS IN ENZYMOLOGY, Academic Press, Inc.; GENE TRANSFER VECTORS FOR MAMMALIAN CELLS, J. H. Miller and M. P. Calos eds. (Cold Spring Harbor Laboratory, 1987); METHODS IN ENZYMOLOGY, Vol. 154 and 155, Wu and Grossman, eds., and Wu, ed., respectively (Academic Press, 1987), IMMUNOCHEMICAL METHODS IN CELL AND MOLECULAR BIOLOGY, R. J. Mayer and J. H. Walker, eds. (Academic Press London, Harcourt Brace U.S., 1987), PROTEIN PURIFICATION: PRINCIPLES AND PRACTICE, 2nd ed. (Springer-Verlag, N.Y. (1987), and HANDBOOK OF EXPERIMENTAL IMMUNOLOGY, Vol. I-IV, D. M. Weir et al., (Blackwell Scientific Publications, 1986); Kitts et al., Biotechniques 14:810-817 (1993); Munemitsu et al., Mol. and Cell. Biol. 10:5977-5982 (1990).

The present invention contemplates keratinocytes and skin equivalents expressing proteinase inhibitor polypeptides, and compositions and methods for making such cells. In some embodiments, host cells are induced to express exogenous polypeptides through transfection with an expression vector containing DNA encoding the exogenous polypeptide. An expression vector containing proteinase inhibitor DNA can be produced by operably linking proteinase inhibitor to one or more regulatory sequences such that the resulting vector is operable in a desired host. Cell transformation procedures suitable for use herein are those known in the art and include, for example with mammalian cell systems, dextran-mediated transfection, calcium phosphate precipitation, polybrene-mediated transfection, protoplast fusion, electroporation, encapsulation of the exogenous polynucleotide in liposomes, and direct microinjection of the DNA into nuclei. In preferred embodiments, cells are transfected with a pUB-Bsd expression vector containing exogenous proteinase inhibitor DNA (e.g., TIMP-1) operably linked to promoter (e.g., K14 or involucrin) DNA.

Immunoassays and activity assays that are known in the art can be utilized herein to determine if the transformed host cells are expressing the desired exogenous polypeptide (e.g., TIMP-1). In some embodiments, detection of intracellular production of proteinase inhibitor polypeptides by transformed host cells is accomplished with an immunofluorescence assay. In preferred embodiments, detection of intracellular production of exogenous polypeptides by transformed host cells is accomplished through a RT-PCR screen. In further embodiments, detection of secreted or extracellular production of proteinase inhibitor by transformed host cells is accomplished through a direct ELISA screen. In some embodiments, the proteinase inhibitor polypeptide is detected by Western blotting.

In other embodiments, expression vectors comprising exogenous polypeptides are introduced directly into tissues (e.g., human skin equivalents). Expression vectors may be introduced into tissues using any suitable technique including, but not limited to, electroporation, particle bombardment (e.g., U.S. Pat. Nos. 6,685,669; 6,592,545; and 6,004,286; each of which is herein incorporated by reference) and transfection.

II. Treatment of Wounds with Keratinocytes Cells Transfected with Exogenous Polypeptides Successful treatment of chronic skin wounds (e.g., venous ulcers, diabetic ulcers, pressure ulcers) is a serious problem. The healing of such a wound often times takes well over a year of treatment. Treatment options currently include dressings and debridement (use of chemicals or surgery to clear away necrotic tissue), and/or antibiotics in the case of infection. These treatment options take extended periods of time and high amounts of patient compliance. As such, a therapy that can increase a practioner's success in healing chronic wounds and accelerate the rate of wound healing would meet an unmet need in the field.

In some embodiments, the present invention contemplates treatment of skin wound with keratinocytes and skin equivalents expressing exogenous proteinase inhibitor.

The present invention contemplates treatment of skin wounds with keratinocytes or skin equivalents expressing proteinase inhibitor polypeptides. In some embodiments, cells expressing proteinase inhibitor polypeptides are topically applied to wound sites. In some embodiments, the keratinocytes are applied via a spray, while in other embodiments, the keratinocytes are applied via a gel. In other embodiments, cells expressing proteinase inhibitor polypeptides are used for engraftment on partial thickness wounds. In other embodiments, cells expressing proteinase inhibitor polypeptides are used for engraftment on full-thickness wounds. In other embodiments, cells expressing proteinase inhibitor polypeptides are used to treat numerous types of internal wounds, including, but not limited to, internal wounds of the mucous membranes that line the gastrointestinal tract, ulcerative colitis, and inflammation of mucous membranes that may be caused by cancer therapies. In still other embodiments, cells expressing proteinase inhibitor polypeptides are used as a temporary or permanent wound dressing.

Cells expressing proteinase inhibitor polypeptides find use in wound closure and burn treatment applications. The use of autografts and allografts for the treatment of burns and wound closure is described in Myers et al., A. J. Surg. 170(1):75-83 (1995) and U.S. Pat. Nos. 5,693,332; 5,658,331; and 6,039,760, each of which is incorporated herein by reference. In some embodiments, the skin equivalents may be used in conjunction with dermal replacements such as DERMAGRAFT. In other embodiments, the skin equivalents are produced using both a standard source of keratinocytes (e.g., NIKS cells) and keratinocytes from the patient that will receive the graft. Therefore, the skin equivalent contains keratinocytes from two different sources. In still further embodiments, the skin equivalent contains keratinocytes from a human tissue isolate. Accordingly, the present invention provides methods for wound closure, including wounds caused by burns, comprising providing cells expressing proteinase inhibitor polypeptides and a patient suffering from a wound and treating the patient with the cells under conditions such that the wound is closed.

Detailed methods for producing the skin equivalents of the present invention are disclosed in the following Experimental section. However, the present invention is not limited to the production of skin equivalents by the methods. Indeed, a variety of organotypic culture techniques may be used to produce skin equivalents, including those described in U.S. Pat. Nos. 5,536,656 and 4,485,096, both of which are incorporated herein by reference. In some embodiments, different populations of keratinocytes are used to construct the skin equivalent. Accordingly, in some embodiments, the skin equivalents of the present invention are formed from keratinocytes derived from an immortalized cell line (e.g., NIKS cells) and cell derived from a patient. In other embodiments, the skin equivalents of the present invention are formed from at least a first population of keratinocytes derived from an immortalized cell line that express a exogenous proteinase inhibitor polypeptide and a second population of keratinocytes derived from an immortalized cell line that do not express a exogenous polypeptide. It is contemplated that varying the ratio of the two populations the dose of proteinase inhibitor delivered can be varied. In still other embodiments, the skin equivalents are formed from at least a first population of keratinocytes expressing a first exogenous proteinase inhibitor polypeptide (e.g., TIMP-1), at least a second population of keratinocytes expressing a second exogenous polypeptide, and/or keratinocytes derived from a patient.

In a further embodiment, the proteinase inhibitor polypeptide or a conjugate thereof can be mixed with a pharmaceutically acceptable carrier to produce a therapeutic composition that can be administered for therapeutic purposes, for example, for wound healing, and for treatment of hyperproliferative diseases of the skin and tumors, such as psoriasis and basal cell carcinoma.

In still further embodiments, the cells expressing proteinase inhibitor polypeptides are engineered to provide a therapeutic agent to a subject. The present invention is not limited to the delivery of any particular therapeutic agent. Indeed, it is contemplated that a variety of therapeutic agents may be delivered to the subject, including, but not limited to, enzymes, peptides, peptide hormones, other proteins, ribosomal RNA, ribozymes, and antisense RNA. These therapeutic agents may be delivered for a variety of purposes, including but not limited to the purpose of correcting genetic defects. In some particular preferred embodiments, the therapeutic agent is delivered for the purpose of detoxifying a patient with an inherited inborn error of metabolism (e.g., aninoacidopathesis) in which the graft serves as wild-type tissue. It is contemplated that delivery of the therapeutic agent corrects the defect. In some embodiments, the cells expressing proteinase inhibitor polypeptides are transfected with a DNA construct encoding a therapeutic agent (e.g., insulin, clotting factor IX, erythropoietin, etc) and the cells grafted onto the subject. The therapeutic agent is then delivered to the patient's bloodstream or other tissues from the graft. In preferred embodiments, the nucleic acid encoding the therapeutic agent is operably linked to a suitable promoter. The present invention is not limited to the use of any particular promoter. Indeed, the use of a variety of promoters is contemplated, including, but not limited to, inducible, constitutive, tissue specific, and keratinocyte specific promoters. In some embodiments, the nucleic acid encoding the therapeutic agent is introduced directly into the keratinocytes (i.e., by calcium phosphate co-precipitation or via liposome transfection). In other preferred embodiments, the nucleic acid encoding the therapeutic agent is provided as a vector and the vector is introduced into the keratinocytes by methods known in the art. In some embodiments, the vector is an episomal vector such as a plasmid. In other embodiments, the vector integrates into the genome of the keratinocytes. Examples of integrating vectors include, but are not limited to, retroviral vectors, adeno-associated virus vectors, and transposon vectors.

III. Testing Methods

The host cells and cultured skin tissue of the present invention may be used for a variety of in vitro tests. In particular, the host cells and cultured skin tissue find use in the evaluation of: skin care products, drug metabolism, cellular responses to test compounds, wound healing, phototoxicity, dermal irritation, dermal inflammation, skin corrosivity, and cell damage. The host cells and cultured skin tissue are provided in a variety of formats for testing, including 6-well, 24-well, and 96-well plates. Additionally, the cultured skin tissue can be divided by standard dissection techniques and then tested. The cultured skin tissue of the present invention may have both an epidermal layer with a differentiated stratum corneum and dermal layer that includes dermal fibroblasts. As described above, in preferred embodiments, the epidermal layer is derived from immortalized NIKS cells. Other preferred cell lines, including NIKS cells are characterized by; i) being immortalized; ii) being nontumorigenic; iii) forming cornified envelopes when induced to differentiate; iv) undergoing normal squamous differentiation in organotypic culture; and v) maintaining cell type-specific growth requirements, wherein said cell type-specific growth requirements include 1) exhibition of morphological characteristics of normal human keratinocytes when cultured in standard keratinocyte growth medium in the presence of mitomycin C-treated 3T3 feeder cells; 2) dependence on epidermal growth factor for growth; and 3) inhibition of growth by transforming growth factor $\beta 1$.

The present invention encompasses a variety of screening assays. In some embodiments, the screening method comprises providing a host cell or cultured skin tissue of the present invention and at least one test compound or product (e.g., a skin care product such as a moisturizer, cosmetic, dye, or fragrance; the products can be in any from, including, but not limited to, creams, lotions, liquids and sprays), applying the product or test compound to the host cell or cultured skin tissue, and assaying the effect of the product or test compound on the host cell or cultured skin tissue. A wide variety of assays are used to determine the effect of the product or test compound on the cultured skin tissue. These assays include, but are not limited to, MTT cytotoxicity assays (Gay, The Living Skin Equivalent as an In Vitro Model for Ranking the Toxic Potential of Dermal Irritants, Toxic. In Vitro (1992)) and ELISA to assay the release of inflammatory modulators (e.g., prostaglandin E2, prostacyclin, and interleukin-1-alpha) and chemoattractants. The assays can be further directed to the toxicity, potency, or efficacy of the compound or product. Additionally, the effect of the compound or product on growth, barrier function, or tissue strength can be tested.

In particular, the present invention contemplates the use of host cells or cultured skin tissue for high throughput screening of compounds from combinatorial libraries (e.g., libraries containing greater than $10^4$ compounds). In some embodiments, the cells are used in second messenger assays that monitor signal transduction following activation of cell-surface receptors. In other embodiments, the cells can be used in reporter gene assays that monitor cellular responses at the transcription/translation level. In still further embodiments, the cells can be used in cell proliferation assays to monitor the overall growth/no growth response of cells to external stimuli.

In second messenger assays, host cells or cultured skin tissue is treated with a compound or plurality of compounds (e.g., from a combinatorial library) and assayed for the presence or absence of a second messenger response. In some preferred embodiments, the cells (e.g., NIKS cells) used to create cultured skin tissue are transfected with an expression vector encoding a recombinant cell surface receptor, ion-channel, voltage gated channel or some other protein of interest involved in a signaling cascade. It is contemplated that at least some of the compounds in the combinatorial library can serve as agonists, antagonists, activators, or inhibitors of the protein or proteins encoded by the vectors. It is also contemplated that at least some of the compounds in the combinatorial library can serve as agonists, antagonists, activators, or inhibitors of protein acting upstream or downstream of the protein encoded by the vector in a signal transduction pathway.

In some embodiments, the second messenger assays measure fluorescent signals from reporter molecules that respond to intracellular changes (e.g., $Ca^{2+}$ concentration, membrane potential, pH, IP3, cAMP, arachidonic acid release) due to stimulation of membrane receptors and ion channels (e.g., ligand gated ion channels; see Denyer et al., Drug Discov. Today 3:323-32 [1998]; and Gonzales et al., Drug. Discov. Today 4:431-39 [1999]). Examples of reporter molecules include, but are not limited to, FRET (florescence resonance energy transfer) systems (e.g., Cuo-lipids and oxonols, EDAN/DABCYL), calcium sensitive indicators (e.g., Fluo-3, FURA 2, INDO 1, and FLUO3/AM, BAPTA AM), chloride-sensitive indicators (e.g., SPQ, SPA), potassium-sensitive indicators (e.g., PBFI), sodium-sensitive indicators (e.g., SBFI), and pH sensitive indicators (e.g., BCECF).

In general, the cells comprising cultured skin tissue are loaded with the indicator prior to exposure to the compound. Responses of the host cells to treatment with the compounds can be detected by methods known in the art, including, but not limited to, fluorescence microscopy, confocal microscopy (e.g., FCS systems), flow cytometry, microfluidic devices, FLIPR systems (See, e.g., Schroeder and Neagle, J. Biomol. Screening 1:75-80 [1996]), and plate-reading systems. In some preferred embodiments, the response (e.g., increase in fluorescent intensity) caused by compound of unknown activity is compared to the response generated by a known agonist and expressed as a percentage of the maximal response of the known agonist. The maximum response caused by a known agonist is defined as a 100% response. Likewise, the maximal response recorded after addition of an agonist to a sample containing a known or test antagonist is detectably lower than the 100% response.

The host cells and cultured skin tissue of the present invention are also useful in reporter gene assays. Reporter gene assays involve the use of host cells transfected with vectors encoding a nucleic acid comprising transcriptional control elements of a target gene (i.e., a gene that controls the biological expression and function of a disease target or inflammatory response) spliced to a coding sequence for a reporter gene. Therefore, activation of the target gene results in activation of the reporter gene product. This serves as indicator of response such an inflammatory response. Therefore, in some embodiments, the reporter gene construct comprises the 5' regulatory region (e.g., promoters and/or enhancers) of a protein that is induced due to skin inflammation or irritation or protein that is involved in the synthesis of compounds produced in response to inflammation or irritation (e.g., prostaglandin or prostacyclin) operably linked to a reporter gene. Examples of reporter genes finding use in the present invention include, but are not limited to, chloramphenicol transferase, alkaline phosphatase, firefly and bacterial luciferases, β-galactosidase, β-lactamase, and green fluorescent protein. The production of these proteins, with the exception of green fluorescent protein, is detected through the use of chemiluminescent, calorimetric, or bioluminecent products of specific substrates (e.g., X-gal and luciferin). Comparisons between compounds of known and unknown activities may be conducted as described above.

In other preferred embodiments, the host cells or cultured skin tissue find use for screening the efficacy of drug introduction across the skin or the affect of drugs directed to the skin. In these embodiments, cultured skin tissue or host cells are treated with the drug delivery system or drug, and the permeation, penetration, or retention or the drug into the skin equivalent is assayed. Methods for assaying drug permeation are provided in Asbill et al., Pharm Res. 17(9): 1092-97 (2000). In some embodiments, cultured skin tissue is mounted on top of modified Franz diffusion cells. The cultured skin tissue is allowed to hydrate for one hour and then pretreated for one hour with propylene glycol. A saturated suspension of the model drug in propylene glycol is then added to the cultured skin tissue. The cultured skin tissue can then be sampled at predetermined intervals. The cultured skin tissue is then analyzed by HPLC to determine the concentration of the drug in the sample. Log P values for the drugs can be determined using the ACD program (Advanced Chemistry Inc., Ontario, Canada). These methods may be adapted to study the delivery of drugs via transdermal patches or other delivery modes.

It is contemplated that cultured skin tissue of the present invention is also useful for the culture and study of tumors that occur naturally in the skin as well as for the culture and study of pathogens that affect the skin. Accordingly, in some embodiments, it contemplated that the cultured skin tissue of the present invention is seeded with malignant cells. By way of non-limiting example, the cultured skin tissue can be seeded with malignant SCC13y cells as described in U.S. Pat. No. 5,989,837, which is incorporated herein by reference, to provide a model of human squamous cell carcinoma. These seeded cultured skin tissue can then be used to screen compounds or other treatment strategies (e.g., radiation or tomotherapy) for efficacy against the tumor in its natural environment. Thus, some embodiments of the present invention provide methods comprising providing cultured skin tissue comprising malignant cells or a tumor and at least one test compound, treating the cultured skin tissue with the compound, and assaying the effect of the treatment on the malignant cells or tumors. In other embodiments of the present invention, methods are provided that comprise providing cultured skin tissue comprising malignant cells or a tumor and at least one test therapy (e.g., radiation or phototherapy, treating the cultured skin tissue with the therapy, and assaying the effect of the therapy on the malignant cells or tumors.

In other embodiments, cultured skin tissue is used to culture and study skin pathogens. By way of non-limiting example, cultured skin tissue is infected with human papilloma virus (HPV) such as HPV18. Methods for preparing cultured skin tissue infected with HPV are described in U.S. Pat. No. 5,994,115, which is incorporated herein by reference. Thus, some embodiments of the present invention provide methods comprising providing cultured skin tissue infected with a pathogen of interest and at least one test compound or treatment and treating the cultured skin tissue with the test compound or treatment. In some preferred embodiments, the methods further comprise assaying the effect the test compound or treatment on the pathogen. Such assays may be conducted by assaying the presence, absence, or quantity of the pathogen in the cultured skin tissue following treatment. For example, an ELISA may be performed to detect or quantify the pathogen. In some particularly preferred embodiments, the pathogen is viral pathogen such as HPV.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: eq (equivalents); M (Molar); μM (micromolar); N (Normal); mol (moles); mmol (millimoles); μmol (micromoles); mnol (nanomoles); g (grams); mg (milligrams); μg (micrograms); ng (nanograms); 1 or L (liters); ml (milliliters); μl (microliters); cm (centimeters); mm (millimeters); μm (micrometers); nm (nanometers); ° C. (degrees Centigrade); U (units), mU (milliunits); min. (minutes); sec. (seconds); % (percent); kb (kilobase); bp (base pair); PCR (polymerase chain reaction); BSA (bovine serum albumin); Pfu (Pyrococcus furiosus).

Example 1

TIMP-1 DNA Construct Generation and Transient Transfection of NIKS Keratinocytes This Example describes the construction of NIKS cells expressing TIMP-1.

Figure 3:
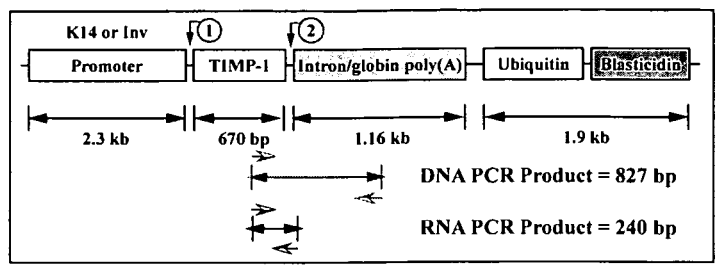
FIG. 3 shows TIMP-1 Expression construct design using either the K14 or involucrin promoter.

Cultures: A construct was generated in which expression of TIMP-1 is driven by the keratin-14 (K14) promoter (FIG. 3). Transient transfection experiments were conducted to verify transgene expression within NIKS keratinocytes. TIMP-1 cDNA was isolated by PCR using commercially available cDNAs (Clontech, Palo Alto, Calif.) and primers based on the published TIMP-1 sequence (GenBank Accession #X03124). The primers were designed to add Not I and Sal I restriction sites to the 5' and 3' ends respectively. Not I and Sal I digests were used to excise the TIMP-1 cDNA from the pCR2.1-TOPO expression vector (Invitrogen, Carlsbad, Calif.) carrying the amplified gene. TIMP-1 cDNA was then ligated into a K14 promoter-containing expression vector. This expression plasmid was confirmed by restriction analysis and DNA sequencing (UW Biotechnology Center). The final TIMP-1 construct was prepared for transfection into mammalian cells using an Endotoxin-Free Maxiprep Kit (Qiagen, Valencia, Calif.). NIKS keratinocytes were plated at a density of $4 \times 10^5$ cells onto 60 mm dishes. After a 24 hour incubation at 37° C. under 5% $CO_2$ (approximately 50% confluence), keratinocyte cultures were transfected with TransIt liposomal transfection reagent (Mirus, Madison, Wis.). A total of 4 μg DNA and 12 μl TransIt was delivered in 200 μl F-12 medium per 60 mm plate. Control plates were either mock transfected (TransIt and F12 only) or were transfected with empty expression vector (K14 promoter-containing expression vector). Empty vector transfection was used to ensure that the vector itself did not alter protein production.

Detection of TIMP-1 mRNA Expression in Transiently-Transfected Cultures: Reverse transcription PCR (RT-PCR) was used to detect transgene expression in transiently-transfected NIKS cells. As depicted in FIG. 3, the forward primer was designed to anneal to the transgene coding region and the reverse primer was designed to anneal to a vector sequence from the rabbit β-globin gene. This primer design allowed one to distinguish transgene mRNA from DNA because the primers span an intron in the β-globin fragment. Since one primer anneals to the rabbit β-globin fragment, this primer set did not amplify endogenous TIMP-1 mRNA. Using this strategy, endogenous TIMP-1 mRNA (240 bp) was readily distinguished from PCR products amplified from expression vector DNA (827 bp).

Figure 4:
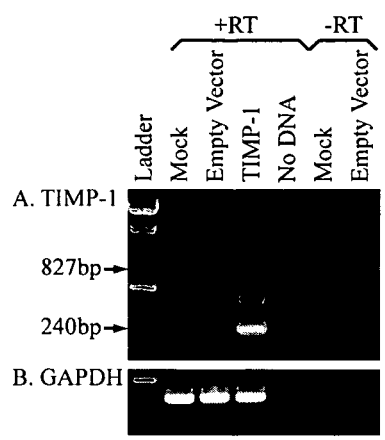
FIG. 4 show reverse-transcription PCR of transiently-transfected NIKS keratinocytes.

Twenty-four hours after transfection, total RNA was isolated (TRIzol Reagent, Invitrogen, Carlsbad, Calif.) from 60-70% confluent cultures of mock transfected NIKS and NIKS cells transiently-transfected with either empty vector or TIMP-1-containing plasmids. Samples were treated with DNase I to remove contaminating DNA (Promega, Madison, Wis.) and reverse transcribed (M-MLV RT, Invitrogen, Carlsbad, Calif.) using oligo dT primer. PCR products were visualized by agarose gel electrophoresis. As shown in FIG. 4, exogenous TIMP-1 mRNA (240 bp) was detected in NIKS cells transfected with the TIMP-1-containing vector but was not detected in either mock or empty vector-transfected cells (FIG. 4A). A faint band at 827 bp was detected in transfected cells from residual expression vector DNA due to incomplete DNase treatment. Primers specific for GAPDH RNA, a product of 375 bp, were used as a loading control (FIG. 4B).

Figure 5:
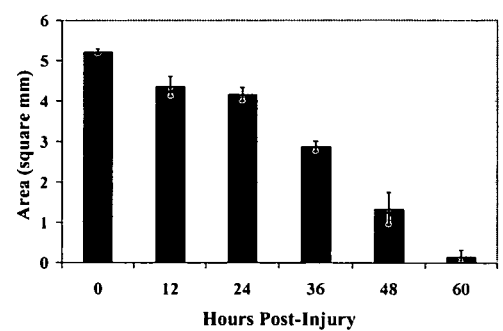
FIG. 5 shows migration of NIKS keratinocytes in monolayer culture.

Exogenous TIMP-1 Expression and Migration of NIKS Keratinocytes: A quantitative migration assay was used to measure the ability of NIKS keratinocytes to re-epithelialize a tissue-culture-treated surface [Kim et al., Cancer Res, 2003. 63(17): p. 5454-61]. Studies have shown that TIMP-1 overexpression may hinder cell migration under certain circumstances [Pilcher et al., J Cell Biol, 1997. 137(6): p. 1445-57; Salonurmi et al., Cell Tissue Res, 2003]. Monolayer cultures were evaluated using this assay to establish the baseline migration rate of NIKS cells. Briefly, confluent cells were treated with mitomycin C (25 μg/ml) for 1 hour to inactivate cellular proliferation. A 2 mm wide injury line was scraped on the culture plate and cells were incubated with growth medium until fixed. Micrographs (5 independent fields) were taken of injured sites and the injury size per field ($mm^2$) was calculated using imaging software (NIH Image 1.62). The injured area was plotted as a function of time to determine the extent of keratinocyte migration (FIG. 5). NIKS keratinocytes fully re-epithelialized the injured area in approximately 60 hours.

Isolation and Characterization of Stably-Transfected NIKS Keratinocytes: Stable clones of NIKS keratinocytes containing the K14-VEGF expression construct ($NIKS^{VEGF}$) have been successfully isolated. These clones were obtained by transfecting NIKS cells and selecting clones of stably-transfected cells by growth in medium containing blasticidin. $NIKS^{VEGF}$ genomic DNA was amplified with specific primers to verify the presence of the appropriate expression construct. RT-PCR analysis of multiple independent $NIKS^{VEGF}$ clones confirmed that these clones specifically overexpressed the $VEGF_{165}$ isoform compared to endogenous VEGF levels.

Expression and Secretion of VEGF from Transgenic Skin Tissue: The expression of $VEGF_{165}$ mRNA was examined by RT-PCR in skin tissue generated from stable clones. Total RNA was extracted and subjected to RT-PCR using primers that detected mRNA expressed from the $VEGF_{165}$ transgene, but not from the endogenous VEGF gene. Transgene-specific VEGF mRNA was detected in skin tissue prepared from $NIKS^{VEGF}$ clones, but was not detected in RNA from skin tissue prepared from untransfected NIKS cells.

Figure 6:
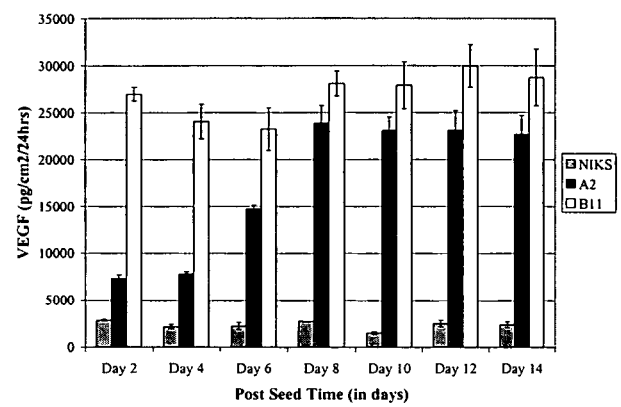
FIG. 6 shows VEGF protein expression in stable clones over time.

To assess VEGF secretion from transgenic skin tissue, two $NIKS^{VEGF}$ clones were cultured organotypically in parallel with untransfected NIKS control cultures. Conditioned media samples were collected periodically after cells were seeded onto the dermal equivalent. FIG. 6 shows VEGF content, as determined by ELISA, at each timepoint. Elevated levels of VEGF protein were observed in $NIKS^{VEGF}$ tissues as compared to untransfected NIKS tissues at all timepoints.

Figure 7:
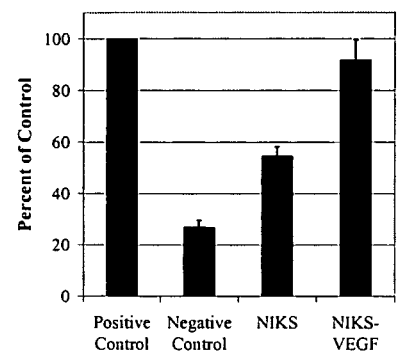
FIG. 7 shows that conditioned medium from NIKS$^{VEGF}$ cells stimulate growth of HMVEC cells.

Bioactivity of Secreted VEGF: VEGF is a potent mitogen for human microvascular endothelial cells (HMVECs). To determine if the elevated levels of VEGF detected in media from $NIKS^{VEGF}$ tissues could stimulate proliferation of HMVECs, these cells were cultured in the presence of conditioned medium (containing control basal medium) from either NIKS or $NIKS^{VEGF}$ organotypic cultures for 6 days. Endothelial cell growth medium fully supplemented with growth factors was used as a positive control, unsupplemented basal medium acted as a negative control. The number of HMVEC cells was counted and reported as a percentage of the controls, with the positive control set to 100%. The results, shown in FIG. 7, demonstrate that conditioned medium from $NIKS^{VEGF}$ cells had a stimulatory effect on HMVEC proliferation, likely due to elevated levels of secreted VEGF.

As demonstrated by the results shown above, the $NIKS^{VEGF}$ cells are capable of secreting this biologically active protein from fully-formed, transgenic skin tissue. These results demonstrate that skin tissue can be engineered to express and secrete specific, bioactive proteins.

Example 2

Design and Construction of Human TIMP-1 Expression Vectors

This Example describes the generation of expression vectors for expression of TIMP-1 in keratinocytes.

Expression Vector Construction: Transgenic constructs are created containing the TIMP-1 gene driven by either the K14 or, as an alternative strategy, the involucrin promoter cloned into the pUb-Bsd expression vector (Invitrogen, Carlsbad, Calif.) (FIG. 3). This vector contains a drug selection cassette that utilizes the ubiquitin promoter driving blasticidin gene expression [Deng et al., Biotechniques, 1998. 25(2): p. 274-80]. As described in Example 1, this drug selection strategy has been successfully used to produce genetically-modified NIKS clonal cell lines capable of regenerating normal epidermal architecture. The human K14 promoter directs constitutive tissue-specific expression in keratinocytes of the basal epidermal layer. The human involucrin promoter targets expression to non-proliferating, suprabasal keratinocytes. The integrity of the cloned promoter PCR products are confirmed by restriction enzyme analysis and DNA sequencing using K14- or involucrin-specific primers. It has been demonstrated that use of both the K14 and involucrin promoters supports expression in both monolayer and organotypic cultures of NIKS keratinocytes.

The K14-TIMP-1 expression construct has been assembled and confirmed (see Example 1). The coding region for TIMP-1 was inserted downstream from the K14 promoter and a DNA fragment containing the rabbit β-globin intron and poly(A) signal was inserted downstream of the TIMP-1 coding region. Assembly of the construct using the involucrin promoter for TIMP-1 expression is completed in a similar fashion. In addition to these expression constructs, vectors are made containing the commonly used influenza hemagglutinin (HA) epitope tag (Clontech, Palo Alto, Calif.) to assist in exogenous protein identification. HA tags have been used successfully in numerous expression systems [Flanagan-Steet et al., Dev Biol, 2000. 218(1): p. 21-37; Lee et al., J Biol Chem, 2001. 276(39): p. 36404-10; Donelson Smith et al., The Journal of Biological Chemistry, 1999. 274(28): p. 19894-19900; Wang et al., Mol Cell Biol, 1999. 19(6): p. 4008-18.]. Constructs contain localization of the epitope tag to both the N-terminal and C-terminal ends of the protein (FIG. 3). Appropriate empty vector constructs are also generated. Accuracy of all plasmids is confirmed by restriction analysis and DNA sequencing.

These vectors are used for the transient transfection of NIKS keratinocytes and subsequent expression studies. Expression strategies resulting in non-functional TIMP-1 protein are eliminated from further analysis. Successful vectors are used in the generation and evaluation of stable transfectants.

Transient Transfection of NIKS Cells in Monolayer Culture: Purified expression vector DNA is introduced into NIKS cells using TransIt-Keratinocyte reagent (Mirus, Madison, Wis.) as described in Example 1. Mock transfected or empty vector (no TIMP-1) transfected populations of NIKS cells are prepared as controls for transgenic-specific assays such as RT-PCR. Mock or empty vector transfected cells are also used to determine endogenous TIMP-1 protein levels in NIKS keratinocytes.

Assay for TIMP-1 mRNA Expression Levels: All transfected cultures are assayed for mRNA expression levels as described in Example 1 approximately 24 hrs post-transfection to verify transgene expression. Primers designed to span an intron in the rabbit β-globin fragment result in transgene-specific DNA and mRNA PCR products that are 827 bp and 240 bp respectively (see FIG. 3). A separate set of primers that amplifies the entire length of TIMP-1 cDNA is used to detect total TIMP-1 (transgenic and endogenous).

Assay for TIMP-1 Protein Expression Levels: Culture medium from transiently-transfected cells is assayed for TIMP-1 protein production. Immunoblot analysis utilizing specific TIMP-1 antibodies (Oncogene Research Products, San Diego, Calif.) is employed to detect TIMP-1. HA-specific immunoblotting allows for confirmation of exogenous TIMP-1 expression in samples transfected with the tagged expression constructs. To confirm expression of non-tagged, exogenous TIMP-1, a comparison is made to endogenous TIMP-1 levels from non-transfected and empty vector transfected NIKS cells. Recombinant TIMP-1 serves as a positive control (Oncogene Research Products, San Diego, Calif.).

A commercially available human TIMP-1-specific ELISA assay (Amersham Biosciences, Piscataway, N.J.) is used to quantify total TIMP-1 protein. To confirm elevated protein levels in samples transfected with transgenic TIMP-1, a comparison is made to the baseline, endogenous TIMP-1 levels from non-transfected and empty vector transfected NIKS cells.

If elevated levels of TIMP-1 protein are not detected in medium from transiently-transfected NIKS cultures by immunoblot analysis, this finding would suggest that transgenic TIMP-1 may not be freely secreted into the culture medium. This is unlikely based on the report of Petersen et al. [Petersen et al., J Invest Dermatol, 1989. 92(2): p. 156-9], which found that endogenous TIMP-1 is secreted into conditioned media of human keratinocytes. Cell lysates are used for analysis if the TIMP-1 protein remains associated with the outer membranes of the cells rather than being secreted into culture medium.

Example 3

Proteinase Inhibition Activity, Growth-Promoting Activity, and Migration Characteristics of Transiently-Transfected NIKS Cell Monolayer Cultures This Example describes the analysis of NIKS cells transiently-transfected with TIMP-1 expression vectors for exogenous TIMP-1 mRNA expression, total TIMP-1 protein expression, and bioactivity of expressed TIMP-1.

Proteinase Inhibition Assay: To determine if expressed TIMP-1 exhibits increased proteinase inhibition activity, culture medium from cells transiently-transfected with the TIMP-1 expression construct is assayed using the EnzChek Gelatinase/Collagenase Assay (Molecular Probes, Eugene, Oreg.). The EnzChek assay provides a rapid, highly sensitive, fluorescent output method using a fluorescent plate reader to detect the presence of inhibitors in aqueous solutions. The substrate, DQ gelatin, fluoresces only when cleaved by an enzyme providing for a more accurate measurement of protease activity. This is in contrast to the conventional azocoll assay where baseline measurements must be made to circumvent the insolubility of the substrate. Commercially available active MMP-1 or MMP-9 (Calbiochem, San Diego, Calif.) is added at known concentrations to the assay suspension (Sigma, St. Louis, Mo.). Samples of conditioned medium from TIMP-1, empty vector, or untransfected NIKS cells are then added to the proteinase/substrate suspension and the extent of MMP inhibition is determined. Synthetic MMP-1 and MMP-9 specific inhibitors are used as positive controls (Calbiochem, San Diego, Calif.) and TIMP-1 neutralizing antibody (R&D Systems, Minneapolis, Minn.) is added as a specificity control.

Growth Promotion Assay: To determine if TIMP-1 from transiently-transfected NIKS cells exhibits growth promotion activity, an assay designed to detect cell growth differences in vitro is utilized [Hayakawa et al., FEBS Lett, 1992. 298(1): p. 29-32]. Normal human keratinocytes (Cambrex, East Rutherford, N.J.) are maintained for five days in serum-free, minimal growth medium or in minimal growth medium supplemented 1:1 with serum-free conditioned medium from TIMP-1, empty vector, or untransfected cells. Serum-free minimal growth medium is used to ensure that exogenous TIMP-1 from serum components does not interfere with this assay. To confirm that TIMP-1 is specifically promoting keratinocyte growth, a TIMP-1 neutralizing antibody (R&D Systems, Minneapolis, Minn.) is added to conditioned media samples. Cell numbers are assessed both by direct, manual counting and through the use of the spectrophotometric MTT assay. Briefly, the MTT substrate is converted to MTT Formazan by mitochondrial enzymatic activity. This product is then extracted into isopropanol and read at 550 nm. The cell numbers generated using the MTT assays are directly compared to the visual cell counts to assess accuracy.

Cellular Migration Assay: As described above, a quantitative assay is used to measure the ability of NIKSTIMP1 keratinocytes to re-epithelialize a tissue-culture-treated surface. Monolayer cultures of NIKSTIMP1 cells are evaluated and compared to the migration rate of empty vector transfected and untransfected NIKS cells.

If it is not possible to detect an increase in bioactivity directly using conditioned medium from transiently-transfected cells, microcon filters (Millipore, Billerica, Mass.) are used to concentrate the conditioned medium samples. If the TIMP-1 protein remains associated with cellular membranes rather than being freely secreted into the cell culture medium, cell lysates are assayed directly.

Example 4

Development of Stable, Genetically-Modified NIKS Cell Clones

This Example described the development of stable NIKS cell clones and the evaluation of bioactivity of TIMP-1 from these stable clones. The transient transfection experiments described above are intended to confirm functionality of the expression constructs and to optimize the required detection and bioactivity assays. In this Example, NIKS cells stably-transfected with TIMP-1 expression vectors are analyzed for exogenous TIMP-1 mRNA expression, total TIMP-1 protein expression, and bioactivity of expressed TIMP-1 using these assays, and specific levels of overexpression are assigned to the $NIKS^{TIMP1}$ clones obtained.

Since high levels of exogenous TIMP-1 could potentially inhibit keratinocyte migration and re-epithelialization, $NIKS^{TIMP1}$ clones expressing a wide range of TIMP-1 levels are examined. This strategy allows for the identification of clones expressing elevated levels of TIMP-1 that do not interfere with normal cellular proliferation or migration. To assist in characterization, clones are grouped by TIMP-1 protein expression levels. Published levels of endogenous TIMP-1 expression for preconfluent, primary human keratinocytes in monolayer culture range from $26\pm2$ ng/$10^5$ cells to $45\pm11$ ng/$10^5$ cells [Petersen et al., J Invest Dermatol, 1989. 92(2): p. 156-9]. Clones expressing TIMP-1 protein levels 2-10 fold of that found in unmodified NIKS are defined as "low expressors". "Medium expressors" are defined as clones exhibiting 10-25 fold excess TIMP-1 protein levels and "high expressors" encompass TIMP-1 expression levels at 25-50 fold endogenous levels.

Clones with a wide range of TIMP-1 protein expression are examined. A comparison of key cellular parameters, such as proliferation and morphology, between $NIKS^{TIMP1}$ clones and the original NIKS cell-line is completed.

Selection and Characterization of Stable Transfectants: To produce genetically-modified NIKS clonal cell lines, purified DNA from the TIMP-1 expression vectors is transfected into NIKS cells using TransIt-Keratinocyte reagent (Mirus, Madison, Wis.). Transfected cells are selected by growth in medium containing blasticidin, which will kill any NIKS cells that have not incorporated the plasmid into their genome. Clonal populations of stably-transfected NIKS cells are isolated by seeding blasticidin-selected transfected cells at low density on a feeder layer of blasticidin-resistant 3T3 cells in tissue culture treated dishes. Putative $NIKS^{TIMP1}$ clones are further characterized by Southern blot analysis using plasmid-derived digoxygenin-labeled probes to reveal gene copy number and confirm that each cell line derives from a different clonal isolate.

Analysis of Stable TIMP-1 mRNA and Protein Expression in Monolayer Culture: To confirm the presence of the TIMP-1 transgene and to assess exogenous TIMP-1 mRNA levels, monolayer cultures of clonal $NIKS^{TIMP1}$ isolates are assayed for mRNA expression levels at several timepoints post-plating as previously described. Using primers and assay conditions previously optimized as described above, TIMP-1 transgene-specific PCR products generated from spliced RNA templates results in fragments 600 bp smaller than the corresponding fragments amplified from DNA. The anticipated PCR product specific for the TIMP-1 transgene mRNA product is 240 bp (FIG. 3).

$NIKS^{TIMP1}$ clones previously confirmed by RT-PCR are assayed for TIMP-1 protein production as described above. Culture medium from clonal isolates in monolayer culture is assayed and compared to endogenous TIMP-1 levels from non-transfected NIKS cells and to NIKS cells stably-transfected with the empty vector construct. Analysis utilizing the HA epitope tag is completed for cells stably-transfected with tagged expression constructs. $NIKS^{TIMP1}$ clones are grouped by TIMP-1 protein expression levels as described above.

Proteinase Inhibition, Growth Promotion, and Cellular Migration Analysis for $NIKS^{TIMP1}$ Clones in Monolayer Culture: To screen the clonal isolates for biological activity, culture medium from $NIKS^{TIMP1}$ clones in monolayer culture is assayed for TIMP-1 bioactivity as described above. Conditioned media, concentrated conditioned media, or cell lysates from $NIKS^{TIMP1}$ clones is used as necessary. To detect elevated TIMP-1 bioactivity levels, a comparison is made to both endogenous TIMP-1 levels from non-transfected NIKS cells and to NIKS cells stably-transfected with the empty vector construct. The level of proteinase inhibition activity for each clonal isolate is determined. Since cell migration and replication are tightly linked in monolayer culture of keratinocytes, it is not expected that $NIKS^{TIMP1}$ clones that exhibit aberrant migration characteristics will be isolated [Barrandon and Green, Cell, 1987. 50(7): p. 1131-7]. Nonetheless, the migration rate for each clonal isolate is determined as described above. $NIKS^{TIMP1}$ clones expressing levels of TIMP-1 that interfere with normal cellular migration are eliminated from further study.

Example 5

Generation and Analysis of TIMP-1 Expressing Cells

This example describes the generation and analysis of NIKS cells that express TIMP-1.

TIMP-1 Expression Construct Generation

TIMP-1 cDNA was isolated by PCR using commercially available cDNAs (Clontech, Palo Alto, Calif.) and primers based on the published TIMP-1 sequence (GenBank Accession # X03124). For constructs bearing the epitope tag, the appropriate sequence encoding HA was incorporated into either the 5' or 3' primer. Amplified cDNA was inserted into the pCR2.1-TOPO expression vector (Invitrogen, Carlsbad, Calif.) and confirmed by DNA sequencing (UW Biotechnology Center). TIMP-1 cDNA was then transferred into either the K14 promoter-containing or the INV promoter-containing expression vector. The integrity of the final expression plasmids were confirmed by restriction enzyme analysis and DNA sequencing.

The human K14 promoter directs constitutive tissue-specific expression in keratinocytes of the basal epidermal layer. The human involucrin promoter targets expression to non-proliferating, suprabasal keratinocytes. The human K14 promoter and involucrin promoter sequences were isolated using PCR primers based on published sequences (Leask et al., Genes Dev, 1990. 4(11): p. 1985-98). The expression vectors contain the rabbit β-globin intron and the poly(A) signal downstream of the TIMP-1 coding region. Expression vectors also contain a drug selection cassette that utilizes the ubiquitin promoter driving expression of a blasticidin resistance gene expression (Deng et al., Biotechniques, 1998. 25(2): p. 274-80). All vectors used to generate stable clones have had their ampicillin cassette removed as recommended by the FDA.

Figure 10:
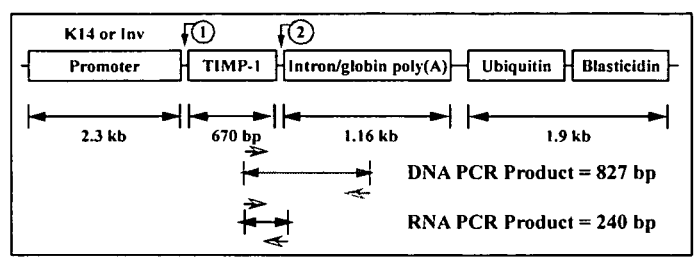
FIG. 10 shows TIMP-1 expression construct design.

Detection of TIMP-1 mRNA Expression in Transiently-Transfected Cultures:

Reverse transcription PCR (RT-PCR) was used to detect transgene expression in transiently-transfected NIKS cells. As depicted in FIG. 10, the forward primer was designed to anneal to the TIMP-1 coding region and the reverse primer was designed to anneal to a vector sequence from the rabbit β-globin gene. This primer design allowed one to distinguish transgene mRNA from DNA because the primers span an intron in the β-globin fragment. Since one primer anneals to the rabbit β-globin fragment, this primer set did not amplify endogenous TIMP-1 mRNA. Using this strategy, exogenous TIMP-1 mRNA (240 bp) was readily distinguished from PCR products amplified from expression vector DNA (827 bp).

Twenty-four hours after transfection, total RNA was isolated (TRIzol Reagent, Invitrogen, Carlsbad, Calif.) from 60-70% confluent cultures of mock transfected NIKS and NIKS cells transiently-transfected with either empty vector or TIMP-1-containing plasmids. Samples were reverse transcribed (M-MLV RT, Invitrogen, Carlsbad, Calif.) using oligo dT primer. PCR products were visualized by agarose gel electrophoresis. Transient transfection of NIKS keratinocytes with HA-tagged TIMP-1 constructs driven by the K14 promoter did not produce RNA expression, even though the coding sequence was verified to be correct. These vectors as well as the untagged K14 and INV TIMP-1 vectors progressed into the generation and evaluation of stable transfectants.

Figure 11:
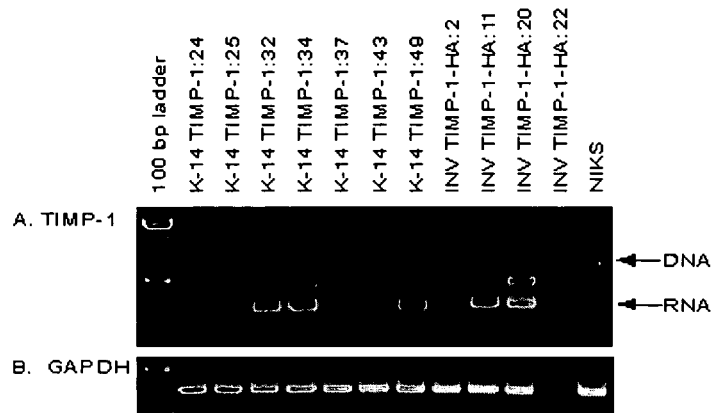
FIG. 11 shows Reverse-transcription PCR of stable NIKSTIMP1 keratinocytes.

Isolation and Characterization of Stably-Transfected NIKS Keratinocytes:

Stable clones of NIKS keratinocytes containing all expression constructs that have demonstrated expression of TIMP-1 in transient transfections have been successfully isolated. These clones were obtained by electroporating NIKS cells using methods known in the art. Transfected cells were selected by growth in medium containing blasticidin, which selected against any NIKS cells that have not incorporated the plasmid into their genome. Clonal populations of stably-transfected NIKS cells were isolated by seeding blasticidin-selected transfected cells at low density on a feeder layer of blasticidin-resistant 3T3 cells in tissue culture treated dishes. Overall, 208 clones were isolated between the four expression constructs. Multiple independent NIKSTIMP1 clones were confirmed to overexpress TIMP-1 compared to untransfected NIKS. Using the RT-PCR analysis exogenous TIMP-1 mRNA (240 bp) was detected in NIKS cells transfected with the TIMP-1-containing vector but was not detected in either mock or empty vector-transfected cells. Primers specific for GAPDH RNA, a product of 375 bp, were used as a loading control. A subset of these is shown in FIG. 11.

Figure 12:
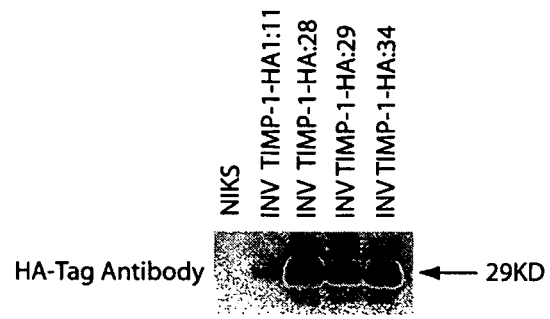
FIG. 12 shows that exogenously expressed TIMP-1 can be detected using HA-antibody.

Exogenous TIMP-1 Expression:

The expression of exogenous TIMP-1 protein from HA-tagged NIKSTIMP1 stable clones in monolayer culture was examined by Western blot. Cell lysates were collected using Cytobuster Reagent (Invitrogen, Carlsbad, Calif.). Protein levels were quantified using a BCA assay (Pierce, Rockford, Ill.). 15 µg of protein was loaded onto a 12% Tris-Glycine gel (Invitrogen, Carlsbad, Calif.) and then transferred to PVDF membrane (Invitrogen, Carlsbad, Calif.). Using the HA-antibody (Roche, Penzberg, Germany) exogenous TIMP-1 protein could be detected in cells transformed with the appropriate vector (FIG. 12). In addition TIMP-1 could be detected in conditioned media ensuring that TIMP-1 was being secreted properly into the media.

To assess TIMP-1 secretion, NIKSTIMP1 clones were cultured in monolayer and conditioned media collected after 24 hrs. Table 3 shows fold TIMP-1 content, as determined by ELISA (R&D Systems, Minneapolis, Minn.) when compared to untransfected NIKS.

Clones with a wide range of TIMP-1 protein expression were examined. From protein levels, isolated clones were then categorized as "low (1-3 fold)," "medium (4-6 fold)," or "high (7-9 fold)" expressors (Table 3).

TABLE 3

| Cells | Concentration (ng/ml)/24 hr. | Standard Deviation | Fold Difference Compared to the NIKS ™ | Ranking |
|---|---|---|---|---|
| NIKS ™ | 38.7 | 5.6 | N/A | N/A |
| K14 TIMP-1:32 | 268.8 | 3.6 | 7.0 | High |
| K14 TIMP-1:34 | 233 | 1.1 | 6.0 | Medium |
| K14 TIMP-1:49 | 88.8 | 10.4 | 2.3 | Low |
| INV HA-TIMP-1:1 | 78.6 | 3.0 | 2.0 | Low |
| INV HA-TIMP-1:19 | 228.1 | 4.9 | 5.9 | Medium |
| INV HA-TIMP-1:34 | 157.1 | 4.7 | 4.1 | Medium |
| INV TIMP-1-HA:11 | 71.5 | 6.6 | 1.9 | Low |
| INV TIMP-1-HA:28 | 248.9 | 8.4 | 6.4 | Medium |
| INV TIMP-1-HA:29 | 121.5 | 10.1 | 3.1 | Low |
| INV TIMP-1-HA:32 | 53.1 | 10.9 | 1.4 | Low |
| INV TIMP-1-HA:34 | 326.3 | 6.0 | 8.4 | High |
| INV TIMP-1-HA:39 | 106.8 | 0.9 | 2.8 | Low |
| INV TIMP-1-HA:41 | 75.1 | 10.1 | 1.9 | Low |

Migration of NIKS Keratinocytes:

A quantitative migration assay was used to measure the ability of NIKS keratinocytes to re-epithelialize a tissue-culture-treated surface (Kim et al., Cancer Res, 2003. 63(17): p. 5454-61). Studies have shown that TIMP-1 overexpression may hinder cell migration under certain circumstances (Pilcher et al., J Cell Biol, 1997. 137(6): p. 1445-57; Salonurmi et al., Cell Tissue Res, 2003). Therefore, this quantitative migration assay was employed. Monolayer cultures were evaluated using this assay to establish the baseline migration rate of NIKS cells and compared to the migration rate of NIKSTIMP1. Briefly, triplicate clone samples of confluent cells were treated with mitomycin C (25 µg/ml) for 1 hour to inactivate cellular proliferation. A 2 mm wide injury line was scraped on the culture plate and cells were incubated with growth medium until fixed at 24, 32, 48, and 56 hrs. Micrographs (2-3 independent fields) were taken of injured sites and the injury size per field ($mm^2$) was calculated using imaging software (NIH Image 1.62). The injured area was plotted as a function of time to determine the extent of keratinocyte migration (Table 4). No clones were shown to interfere with cellular migration using this methodology. All clones displayed enhanced migration over the NIKSTM which was treated in the same manner. The present invention is not limited to a particular mechanism. Indeed, an understanding of the mechanism is not necessary to practice the present invention. Nonetheless, Terasaki et al found that TIMP-2 enhanced the migration of normal human epidermal keratinocytes lending support to the concept that TIMPs may have a role in the promotion of migration in these cells (Terasaki et al., J Dermatol, 2003. 30(3): p. 165-72).

TABLE 4

|  | Migration Rate ($mm^2$/24 hr) | Standard Deviation |
| --- | --- | --- |
| NIKS | 1.43 | 0.07 |
| K14 TIMP-1:32 | 3.64 | 0 |
| K14 TIMP-1:34 | 2.69 | 0.44 |
| INV HA-TIMP-1:19 | 2.99 | 0.51 |
| INV TIMP-1-HA:28 | 2.61 | 0.06 |
| INV TIMP-1-HA:29 | 2.27 | 0.31 |
| INV TIMP-1-HA:32 | 3.43 | 0.12 |
| INV TIMP-1-HA:34 | 2.68 | 0.27 |
| INV TIMP-1-HA:41 | 3.32 | 0.33 |
| INV Empty Vector | 1.99 | 0.22 |

Exogenous TIMP-1 Growth Properties

To determine if TIMP-1 from stable NIKSTIMP1 cells exhibits growth promotion activity, two assays designed to detect cell growth differences in vitro were utilized (Hayakawa et al., supra). Cell numbers were assessed in triplicate both by direct, manual counting and through the use of the spectrophotometric MTT assay. Briefly, the MTT substrate is converted to MTT Formazan by mitochondrial enzymatic activity. This product is then extracted into isopropanol and read at 560 nm. Although not a direct measurement of viable cell number, this assay provides an accurate and quick method to determine relative cell numbers when compared to an appropriate control. Serum-free minimal growth medium was used to ensure that TIMP-1 from serum components do not interfere with this assay. Conditioned media for NIKSTM and NIKSTIMP1 were harvested after 48 hrs and used for both assays.

For direct cell counts, NIKSTM were maintained for five days in serum-free, 1:1 minimal media to conditioned medium from TIMP-1, empty vector, or untransfected cells. For the MTT assay, NIKSTM were maintained in serum-free conditioned media from TIMP-1, empty vector or untransfected cells for three days.

Figure 13:
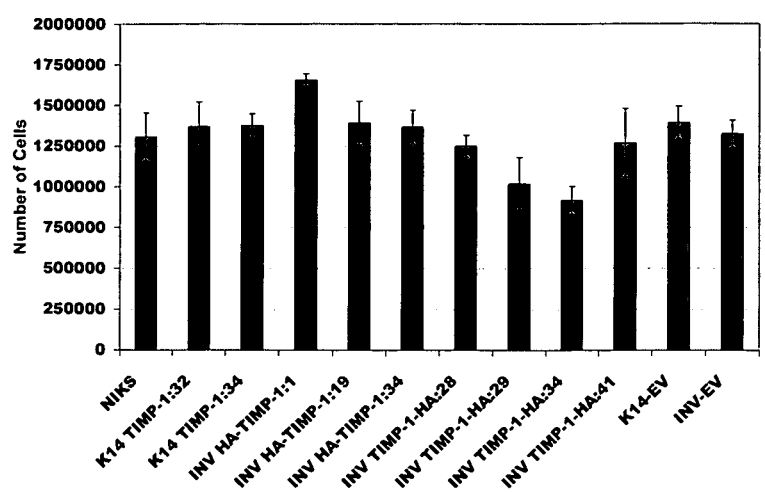
FIG. 13 shows that growth properties of the majority of NIKS$^{TIMP1}$ clones are comparable to NIKS cells.

Direct cell counts in FIG. 13 indicate that conditioned media harvested from TIMP-1 stable clones had comparable growth properties to that of the parental NIKSTM. Furthermore, the MTT assay did not show a difference in the growth of clones versus untransfected NIKS. Recombinant TIMP-1 has been shown to stimulate growth of keratinocytes at a 1-10 µg/ml concentration and stable clones produce nanogram amounts (Bertaux et al, J Invest Dermatol, 1991. 97(4): p. 679-85). The highest expressing clone is currently producing 326 ng/ml per 24 hr period.

Figure 14:
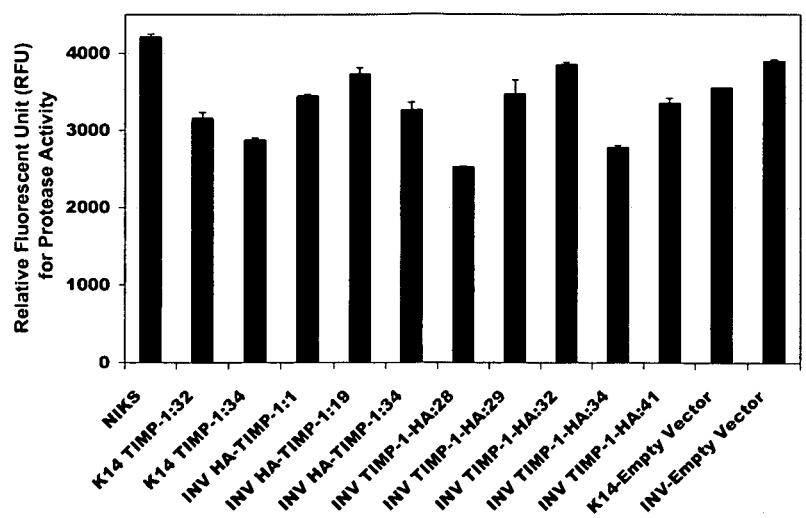
FIG. 14 shows Protease activity of NIKS$^{TIMP1}$ clone conditioned media compared to untransfected NIKS cells.
Figure 15:
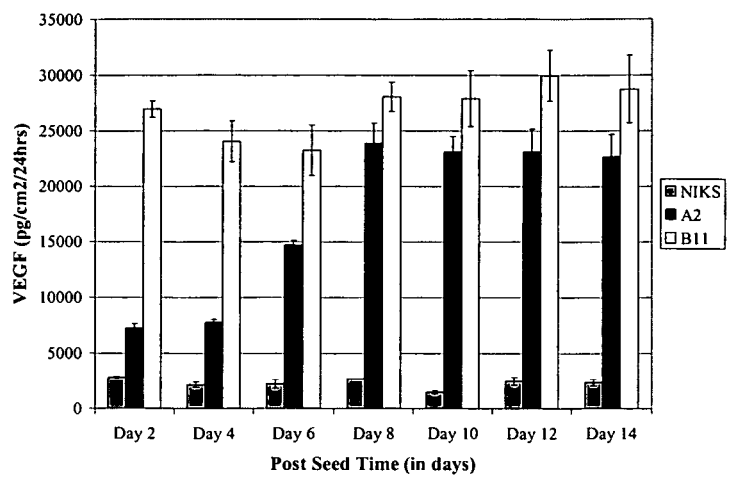
FIG. 15: ELISA measurement of VEGF protein expressed by untransfected NIKS™ and 2 NIKS$^{VEGF}$ clones, A2 and B11. Conditioned media were collected at days 2, 4, 6, 8, 10, 12, and 14 post-plating.

Bioactivity of Secreted TIMP-1:

To confirm that expressed TIMP-1 exhibits increased MMP inhibition activity, conditioned medium from stable TIMP-1 clones was assayed using the EnzChek Gelatinase/Collagenase Assay (Molecular Probes, Eugene, Oreg.). The EnzChek assay provides a rapid, highly sensitive, fluorescent output method using a fluorescent plate reader to detect the extent of proteinase activity in aqueous solutions. The substrate, DQ gelatin, fluoresces only when cleaved by an enzyme providing for a more accurate measurement of protease activity. This is in contrast to the conventional azocoll assay where baseline measurements must be made to circumvent the insolubility of the substrate. Commercially available active MMP-2 (Calbiochem, San Diego, Calif.) was added at known concentrations to the assay suspension (Sigma, St. Louis, Mo.). Replicate samples of 24 hr conditioned medium serum-free from TIMP-1, empty vector, or untransfected NIKS cells were then added to the proteinase/substrate suspension and the extent of MMP inhibition was determined (FIG. 14). The synthetic MMP-2 specific inhibitor 1,10-phenanthroline (Calbiochem, San Diego, Calif.), used as a positive control, inhibited proteinase activity by 30%. Data in FIG. 14 indicates that clone INV TIMP-1-HA:28 displayed as much as a 40% inhibition in MMP-2 protease activity compared to untransfected NIKS. Many other clones displayed robust protease inhibition activity in monolayer in this assay (FIG. 14). Since MMP-2 is not preferentially targeted by TIMP-1 this could indicate the lowest threshold of protease inhibition activity by NIKSTIMP1 clones.

Example 6

Characterization of Properties of NIKSTIMP1 Clones in Organotypic Culture

This Example describes methods for the analysis of clones for their ability to form stratified epidermis, expression levels, and protease inhibition activity.

Preparation of Organotypic Cultures:

NIKSTIMP1 candidate clones expressing a range of TIMP-1 levels and exhibiting protease inhibition in monolayer are used to prepare human skin substitute tissues using organotypic culturing technique and proprietary medium (STRATALIFE medium, StrataTech, Madison, Wis.). Organotypic cultures, comprised of both dermal and epidermal compartments, are prepared as follows.

The dermal compartment is formed by mixing normal human neonatal fibroblasts (Cambrex, East Rutherford, N.J.) with Type I collagen in a Ham's F-12-based medium and allowed to contract. The epidermal compartment is produced by seeding NIKS or NIKSTIMP1 cells on the contracted collagen gel in STRATALIFE medium at an air/medium interface allowing the cultures to be fed from below. Organotypic cultures are incubated at 37° C., 5% $CO_2$, 75% humidity and fed fresh medium every 2 days. By day 10, cells will have stratified to form the basal, spinous, granular and cornified epidermal layers.

Histological sections of skin substitutes tissues formed by NIKSTIMP1 cells are compared to cultures prepared from unmodified NIKS cells. Tissue sections are stained with hematoxylin and eosin to visualize the stratified epidermal layers. Cultures are examined for tissue morphology, and as a more thorough analysis of tissue architecture, immunohistochemistry is performed using a panel of antibodies specific for different stages of keratinocyte differentiation. The distribution of involucrin, P-cadherin, keratin 1, keratin 2e, and transglutaminase within tissue sections is analyzed for proper tissue differentiation. Only those NIKSTIMP1 clones that exhibit normal tissue organization and histology are used in further analysis.

Analysis of TIMP-1 mRNA Expression in Organotypic Cultures:

Skin tissue made from organotypic cultures is assayed for TIMP-1 transgene expression levels in 14 day old cultures using the RNA isolation and the semi-quantitative RT-PCR procedures described above. It is confirmed that the clonal cell lines exhibit a range of expression levels in the context of differentiated skin. QPCR is used for quantitation. qPCR analyzes RNA in real-time, producing a much more quantitative, and therefore, accurate assessment of RNA levels.

Assay for TIMP-1 Protein Expression Levels:

Culture medium from skin tissue produced from stable clones is assayed for TIMP-1 protein production. Immunoblot analysis utilizing specific TIMP-1 antibodies (Oncogene Research Products, San Diego, Calif.) is employed to detect secreted TIMP-1. To confirm expression of exogenous TIMP-1, a comparison is made to endogenous TIMP-1 levels from non-transfected NIKS cells. Recombinant TIMP-1 serves as a positive control (Oncogene Research Products, San Diego, Calif.).

A commercially available human TIMP-1-specific ELISA assay (R&D Systems, Minneapolis, Minn.) is used to quantify total TIMP-1 protein. To confirm elevated protein levels in samples stably transfected with transgenic TIMP-1, a comparison is made to the baseline, endogenous TIMP-1 levels from non-transfected NIKS cells.

Proteinase Inhibition Assay:

To determine if TIMP-1 secreted from tissue is functional, the ability to inhibit proteinase activity is assayed using the EnzChek Gelatinase/Collagenase Assay (Molecular Probes, Eugene, Oreg.). The EnzChek assay provides a rapid, highly sensitive, fluorescent output method using a fluorescent plate reader to detect the presence of inhibitors in aqueous solutions. The substrate, DQ gelatin, fluoresces only when cleaved. Commercially available active MMP-2 (Calbiochem, San Diego, Calif.) is added at known concentrations to the assay suspension (Sigma, St. Louis, Mo.). Samples of conditioned medium from TIMP-1, or untransfected NIKS cells are then added to the proteinase/substrate suspension and the extent of MMP inhibition determined. Synthetic MMP-2 specific inhibitors are used as positive controls (Calbiochem, San Diego, Calif.).

If no increase in bioactivity is observed directly using conditioned medium from organotypics, microcon filters (Millipore, Billerica, Mass.) are used to concentrate the conditioned medium samples. If some of the TIMP-1 protein remains associated with cellular membranes rather than being freely secreted into the cell culture medium, cell lysates are assayed directly.

Example 7

Karyotype and Preliminary Tumorigenicity Studies

This Example describes initial tumorigenicity studies of TIMP-1 expressing NIKS cells.

A preferred aspect of any cell to be used in tissue engineering applications is that they are not tumorigenic. It has previously been demonstrated to the satisfaction of the FDA that NIKS keratinocytes do not form tumors when injected into nude and SCID mice (Allen-Hoffmann et al., Journal of Investigative Dermatology, 2000. 114(3): p. 444-455). To eliminate the possibility that elevated expression of TIMP-1 increases the tumorigenic potential of NIKS cells, several clones are subjected to a soft agar suspension assay. Those that are not tumorigenic in this assay are then injected into nude mice. Animal tumorigenicity studies are performed in two phases. During the first phase, five to ten NIKSTIMP1 clones that exhibit different levels of TIMP-1 expression are injected into five mice each. Clones that do not produce any tumors in the first phase will be injected into a larger number of mice to allow examination of a statistically-significant sample (see below). Any clonal cell line that results in tumor formation following injection is not preferred for clinical development.

Karyotype Analysis:

Karyotypic analysis of NIKSTIMP1 clones is completed to eliminate the rare clones that may have acquired cytogenetic changes during clonal selection. Only clones that exhibit the same stable karyotype as the untransfected NIKS cells are considered for further development.

Soft Agar Assay:

Anchorage-independent growth is highly correlated with tumorigenicity in vivo (Shin et al., Proc Natl Acad Sci USA, 1975. 72(11): p. 4435-9). For this reason, the anchorage-independent growth characteristics of NIKSTIMP1 cells is assayed in agar or methylcellulose-containing medium. Pre-confluent cultures are suspended at $1 \times 10^6$ cells per ml in serum free and additive free 3:1 Ham's F-12/DME and methylcellulose or agar. Cells are photographed in situ in the agar or methylcellulose-containing medium. After 4 weeks NIKSTIMP1 non-tumorigenic cells remain as single cells. The assays are continued for a total of 8 weeks, in order to observe that no slow growing variants of the NIKSTIMP1 cells are made. Untransfected NIKS cells are treated similarly to act as controls.

Preliminary Tumorgenicity Study in Athymic Nude Mice:

Tumorgenicity testing is required by the FDA for cells used in tissue-engineered products. The principal standard for determining the tumorigenic potential of cell lines is a whole animal bioassay procedure. The nude mouse strain offers an excellent animal model to test the tumorigenicity of NIKS cells expressing elevated levels of TIMP-1. A recessive mutation (formerly nu, then later updated to Hfh11nu and most recently to Foxn1nu) in nude mice results in a virtually complete absence of thymic development and offers a rigorous mammalian system in which to study tumorigenic growth in the absence of cell-mediated immunity. The T cell-mediated response of the nude mouse is essentially nonexistent, yet the incidence of spontaneous carcinomas and neoplasms other than those of the immune system is actually no different from that of non-mutant controls and laboratory mice in general (Stutman, Exp Cell Biol, 1979. 47(2): p. 129-35).

Five to ten NIKSTIMP1 clones that have a normal NIKS karyotype are evaluated for tumor formation in five nude mice. Briefly, nude mice (4-5 weeks old) are acclimated for at least one week prior to study initiation. The cells are delivered by subcutaneous injection to both hind flanks of each animal. Animals are injected with 5×10⁶ cells from each clone in 0.1 ml F12 medium per flank. Five negative control animals are injected with 0.1 ml F12 medium per flank. Five positive control animals are injected with 2.5×10⁶ SCC4 cells (human skin squamous cell carcinoma cell line) in 0.1 ml F12 medium per flank.

Mice are examined weekly for tumor formation. Any animals that die prior to the completion of the 12-week study period are thoroughly necropsied to determine cause of death. At the end of the 12-week study period, all animals are sacrificed and photographed. The skin is removed from each animal and the skin surrounding the injection sites is carefully examined for tumors. Skin tissue from each animal is preserved in buffered formalin for future examination.

The presence of any tumors at the sites of injection in mice injected with NIKSTIMP1 cells indicates that these clones are tumorigenic. Clone that do not exhibit tumorgenicity are preferred for further development.

Example 8

Grafting Studies

This Example describes grafting studies using an acute wound model and comparison graft take of EXPRESS-GRAFT Shield skin tissue expressing different levels of TIMP-1 to STRATAGRAFT tissue.

Clones are screened for the ability to promote wound contraction, graft adherence, and vascularization comparable to STRATAGRAFT tissue (Stratatech, Madison, Wis.) in an acute wound model. These parameters are important for healing in both acute and chronic wounds. They also offer tangible endpoints with which graft take can be assessed. Using this Wound model, clones expressing various levels of TIMP-1 are assessed for these wound healing parameters.

Skin tissue expressing different levels of TIMP-1 is grafted onto full-thickness excisional wounds on the backs of athymic nude mice. Four groups of eight animals are grafted with the following skin tissues including NIKSTIMP1 clones.
Group 1—Skin tissue produced from NIKSTM as a control
Group 2—Skin tissue expressing 2-3 fold more TIMP-1 than endogenous levels
Group 3—Skin tissue expressing 4-6 fold more TIMP-1 than endogenous levels
Group 4—Skin tissue expressing 7-8 fold more TIMP-1 than endogenous levels
Graft sites are examined, photographed, and wound area measured at weekly intervals. At two, four, eight, and twelve weeks after grafting, two animals from each group are euthanized. Grafts are excised and a number of parameters relating to graft take, wound healing, and angiogenesis is evaluated as described below.
Tissue Production:

Skin tissue is prepared using the Standard Operating Procedures submitted to the FDA for the production of STRATAGRAFT skin tissue. Tissue is produced in a circular shape with a surface area of 44 cm² and is trimmed to fit the wounds immediately prior to engraftment. Skin tissue expressing TIMP-1 at the levels specified above is prepared by seeding dermal equivalents with NIKSTIMP1 cells and culturing with STRATALIFE media for 14 days. Twenty four hours prior to grafting, TIMP-1 levels are assessed in conditioned media harvested from STRATAGRAFT and NIKSTIMP1 tissue by ELISA to confirm protein ranges. TIMP-1 levels should remain consistent between tissues constructed from the same stable clone.

Graft Histology:

Tissue samples taken from each graft at the time of animal sacrifice are processed for histology and stained with hematoxylin and eosin (H&E) to determine overall tissue architecture. A more thorough analysis of tissue architecture, immunohistochemistry, is performed using a panel of antibodies specific for different stages of keratinocyte differentiation. The distribution of human involucrin, P-cadherin, keratin 1, keratin 2e, and transglutaminase within tissue sections from each experimental group is compared to the control STRATAGRAFT skin tissue.
Grafting Procedures:

All animal procedures are performed in accordance with animal welfare regulations at the University of Wisconsin-Madison. Full-thickness excisional wounds (3×2 cm, 6 cm²) are created on the backs of thirty-two anesthetized athymic nude mice using aseptic techniques. Skin tissue (6 cm²) is placed in the wound bed and secured in place with sutures. The surgical sites are photographed and measured. The grafted areas are covered with non-adherent gauze bandages saturated with antibiotic ointment followed by occlusive and compression dressings. Animals are observed for the 2 hours following recovery from anesthesia to detect any adverse effects of the procedures. Analgesia is administered in accordance with approved protocols. Bandaging is replaced as necessary during the post-operative period. Two weeks after graft placement, bandages are removed from all animals.
Evaluation Criteria for the Acute Wound Model:

Wound Contraction: The area of each graft site is calculated from digital photographs collected at weekly intervals. Wound contraction is calculated for each animal by dividing the wound area at each time point by the initial wound area and is expressed as a percentage of initial wound area. Wound contraction data is compared between groups using a Student's T-test. Differences between groups are considered significant if the p-value is <0.05. Supp et al. used a similar evaluation to quantify wound healing (Supp and Boyce, J Burn Care Rehabil, 2002. 23(1): p. 10-20). Less graft contraction is a reliable indicator of stable engraftment as well as better tissue development.
Graft Adherence:

The grafted area on each animal is evaluated visually for graft take using a three point scale commonly used in evaluation of graft take in human clinical studies (Dr. Michael Schurr, Department of Surgery, University of Wisconsin Hospital). The degree to which the grafted tissue can be moved within the wound bed by gentle manual manipulation is evaluated to assess graft adherence. Grafts that are pink and adherent are assigned two points, grafts that are pink or adherent, but not both are assigned one point, and grafts that are neither pink nor adherent receive no points. The graft take scores from each group are compared using the Cochran-Mantel-Haenszel test. Statistical significance is declared if the two-sided p-value is <0.05.

It is contemplated that some of the skin grafts expressing elevated TIMP-1 levels will exhibit accelerated graft take as evidenced by delayed wound contraction, enhanced graft adherence, or increased vascularization (judged by graft color). Such an outcome will indicate improved or accelerated wound healing due to TIMP-1 expression. It is further contemplated that, by testing clones with a wide range of TIMP-1 expression levels, a threshold level of TIMP-1 expression required for improved wound healing is identified.
Graft Vascularization:

Vascularization ensures that grafted material remains healthy thereby contributing to graft take. TIMPs have been shown to have an effect on endothelial cell migration, and thus vessel formation (Baker et al., J Cell Sci, 2002. 115(Pt 19): p. 3719-27). To ensure that vascularization is not compromised, the extent of tissue vascularization is determined by immunohistochemistry using antibodies against mouse CD31/platelet-endothelial cell adhesion molecule-1 (CD31/PECAM-1, BD PharMingen, San Diego, Calif.). The degree of vascularization is determined by calculating the percentage of the dermal tissue staining positive for CD31/PECAM-1. For each tissue group, the percentage of dermal tissue staining positive is compared to that for STRATAGRAFT tissue. Clones that exhibit comparable vascularization to the NIKSTM control or increased vascularization are preferred for further evaluation.

Example 9

Additional Grafting Studies

This example describes grafting studies using a chronic wound model to compare the rates of wound healing and protease inhibition between EXPRESSGRAFT Shield skin tissue expressing different levels of TIMP-1 and STRATAGRAFT tissue.

This example describes methods to identify clones that 1) generate tissue possessing biologically active TIMP-1 as shown by inhibition of protease activity in wound exudates, and 2) enhance the rate of wound healing. For these studies, skin tissue expressing different levels of TIMP-1 is grafted onto chronic wounds created on the backs of athymic nude rats. The creation of a chronic lesion rat efficacy model has been standardized by the Davidson group (Davidson, Arch Dermatol Res, 1998. 290 Suppl: p. S1-11).

This experimental model is useful to test grafts because the lesion exhibits elevated levels of MMP-1, MMP-3 and MMP-9. The lesion is created using a chemotherapeutic agent, adriamycin, introduced intradermally. The injury is thought to form due to a free radical mechanism caused by the introduction of this agent. 500 µl of a 25 mg/ml dose for a total of 12.5 mg per site causes a dermonecrotic lesion to develop over a 14 day period. In rats the lesions have been shown to persist for greater than 50 days (Davidson, supra). Four groups of eight animals are grafted with skin tissue as follows:
Group 1—Skin tissue expressing endogenous levels of TIMP-1
Group 2—Skin tissue expressing 2-3 fold more TIMP-1 than endogenous levels
Group 3—Skin tissue expressing 4-6 fold more TIMP-1 than endogenous levels
Group 4—Skin tissue expressing 7-8 fold more TIMP-1 than endogenous levels Graft sites are examined, photographed, and the wound area measured at weekly intervals. At one, two, four and eight weeks after grafting, two animals from each group are euthanized and examined. This eight week time frame is selected to be within the time period that the chronic wound is known to persist, as well as to observe any short-term effects from the cell-based therapy. Grafts are evaluated using wound contraction, graft adherence and graft vascularization. Additionally, criteria specifically addressing chronic wound healing including measurement of procollagen, pro-MMP-1 and HSP47 levels, as well as the extent of protease inhibition, are analyzed.

Tissue Production and Grafting Procedures:

Skin tissue is prepared as described above. All animal procedures are performed in accordance with animal welfare regulations. Wounds that model chronic ulcers are created on the backs of thirty-two anesthetized rats using a 500 µl intradermal injection of 25 mg/ml adriamycin. The wound is covered with an absorbent hydrogel based dressing that permits collection of wound exudates to monitor wound status. These samples are used to confirm initial protease levels of the wound (discussed below) and serve as a comparison point for the efficacy of the cell-based gene therapy. After 14 days to allow for the creation of the wound, skin tissue (6 cm$^2$) is placed in the wound bed and secured in place with sutures. Adrimycin-induced wounds sites are photographed and measured. The grafted areas are covered with hydrogel dressings, antibiotic ointment, and compression dressings. Animals are observed frequently in the 2 hours following recovery from anesthesia to detect any adverse effects of the procedures. Analgesia is administered in accordance with approved protocols. Bandaging is replaced as necessary during the postoperative period. Two weeks after graft placement, bandages are removed from all animals.

Evaluation of Efficacy Criteria for the Chronic Wound Model:

Wound Contraction and Graft Adherence:

A reduction in graft contraction is a reliable indicator of stable engraftment as well as better tissue development. Contraction is measured as described above. Briefly, the areas of each graft site are calculated from digital photographs collected at weekly intervals. Wound contraction data is compared between groups using a Student's T-test. Differences between a given group and the NIKS control are considered significant if the p-value is <0.05. Supp et al. used a similar evaluation to quantify wound healing (Supp and Boyce, supra).

Graft adherence is measured as described above. Briefly, the grafted area on each animal is evaluated visually for graft take using a three point scale commonly used in evaluation of graft take in human clinical studies (Dr. Michael Schurr, Department of Surgery, University of Wisconsin Hospital). The graft take scores from each group are compared to control tissue using the Cochran-Mantel-Haenszel test. Statistical significance is declared if the two-sided p-value is <0.05.

It is contemplated that some of the skin grafts expressing elevated TIMP-1 levels will exhibit accelerated graft take as evidenced by delayed wound contraction, enhanced graft adherence, or increased vascularization (judged by graft color). Such an outcome indicates improved or accelerated wound healing due to TIMP-1 expression.

Wound Healing:

Several markers of collagen remodeling have been used in the literature as indicators of chronic ulcer improvement (Davidson, supra; Tarlton et al., Wound Repair Regen, 1999. 7(5): p. 347-55). Fibrillar Type I collagen is normally abundant in the skin. The amount of procollagen is indicative of whether collagen is being stabilized into fibrils. The levels of procollagen can easily be tested from wound exudates or tissue samples using ELISA (Prolagen C, Quidel, Oxon, UK). Additionally, in a deteriorating wound the amount of pro-MMP-1 is high when compared to healing wounds. The levels of pro-MMP-1 present in the wound site are also tested by ELISA (R&D Systems, Minneapolis, Minn.). Decreasing levels of procollagen and pro-MMP-1, indicative of reduced extracellular matrix turnover, should be found in a chronic wound exhibiting evidence of healing. The extent of procollagen and pro-MMP-1 reduction is evaluated by comparing each tissue group to the NIKSTM control. Each NIKSTIMP1 group is then be ranked as either low (10%-20% reduction), medium (20%-30% reduction), or high (30%-50% reduction).

Graft and Wound Bed Histology:

Wound sites are analyzed histologically as described above. Briefly, tissue samples taken from each graft at the time of animal sacrifice are processed for histology and stained with H&E to determine overall tissue architecture. The distribution of involucrin, P-cadherin, keratin 1, keratin 2e, and transglutaminase within the epidermal compartment of tissue sections from each experimental group is compared to the NIKSTM control.

In addition, a fibroblast specific marker, HSP47, is used to evaluate the wound bed. A recent study found that HSP47 staining is much stronger in skin ulcer tissue versus normal tissue (Kuroda and Tajima, J Cutan Pathol, 2004. 31(3): p. 241-6). The level of HSP47 staining in the wound bed of each tissue group is compared to the NIKSTM control. Although not quantitative, a reduction in staining intensity is indicative of healing within the wound bed.

Graft Vascularization:

TIMPs have been shown to have an effect on endothelial cell migration, and thus vessel formation (Baker et al., J Cell Sci, 2002. 115(Pt 19): p. 3719-27). To ensure that vascularization is not compromised, the extent of tissue vascularization is determined by immunohistochemistry using antibodies to rat CD31/PECAM-1 (BD PharMingen, San Diego, Calif.). The degree of vascularization is determined by calculating the percentage of the dermal tissue that stains positive for CD31/PECAM-1. For each tissue group, the percentage of dermal tissue staining positive is compared to that for STRATAGRAFT tissue. Clones that exhibit comparable vascularization to the NIKSTM control or increased vascularization are preferred for further evaluation.

Graft Protease Inhibition:

All chronic wounds are covered with an absorbent hydrogel-based dressing that allows for sampling of wound exudates during creation of the wound state and for sampling of wound exudates during graft exposure. The extent of protease activity is determined by analyzing these samples using the EnzChek Gelatinase/Collagenase Assay (Molecular Probes, Eugene, Oreg.) as described above. Wound exudate samples are taken from all animals at post operative-day seven (POD 7) and again on POD 14. The extent of protease inhibition is determined by comparing samples from each EXPRESSGRAFT Shield tissue group to control STRATAGRAFT tissue. Exudate samples are also be assayed by ELISA, as described above, to obtain corresponding TIMP-1 levels. Tissue performance is determined by the extent of protease inhibition and each tissue group is ranked: low (10%-20% inhibition), medium (20%-30% inhibition), high (30%-50% inhibition).

The use of the chronic wound rat model established by Davidson allows for the evaluation of the efficacy of the TIMP-1 expressing skin substitutes of the present invention in the closest approximation to the human condition. Moreover, it has already been established that the level of MMP-1, MMP-3 and MMP-9 expression is elevated in this lesion making it an ideal experimental model. It is contemplated that some of the grafts prepared with NIKSTIMP1, possibly those having low levels of TIMP-1 expression, will exhibit only a slight decrease in protease activity compared to those having received grafts made with STRATAGRAFT tissue. It is contemplated that protease activity will be low for wounds grafted with NIKSTIMP1 grafts with high levels of TIMP-1.

If it is not possible to reliably measure the protease activity present in the wound through sampling of the wound exudates, the wound tissue is sampled directly through biopsy punch both before and after the creation of the chronic wound. In addition, if PECAM staining is not feasible as an indicator of vascularization for this system, then intravenous injection of FITC-Dextrin prior to sacrifice is employed to visualize vasculature.

Example 10

Safety Studies

This Example describes additional assays for tumorigenicity. Clonal cell lines that do not promote tumor formation following injection are preferred for clinical development.

Analysis of Tumorigenicity of NIKSTIMP1:

Three groups of animals are utilized in this study. All groups contain an equal number of male and female mice. Group I consists of twenty-six mice that are injected with a human squamous cell carcinoma cell line, SCC4, as a positive tumorigenic control. Group II, which consists of fifty animals injected with sterile culture medium, serves as a negative control for the experiment. Group III consist of fifty animals, each of which is injected with $1 \times 10^7$ cells from a NIKSTIMP1 clone that exhibited enhanced protease inhibition and that formed no tumors in the preliminary tumor study. Briefly, nude mice (4-5 weeks old) are acclimated for at least one week prior to study initiation. All animals are weighed immediately prior to injection. The cells are delivered by subcutaneous injection to both hind flanks of each animal. Group I animals are injected with $2.5 \times 10^6$ SCC4 cells in 0.1 ml F12 medium per flank. Group II animals are injected with 0.1 ml F12 medium per flank. Group III animals are with $5 \times 10^6$ NIKSTIMP1 cells in 0.1 ml F12 medium per flank.

Mice are examined weekly for tumor formation and are weighed approximately six weeks after injection. Animals are maintained for 12 weeks following injection and then are weighed, photographed, and thoroughly necropsied. Any animals that die prior to the completion of the 12-week study period are thoroughly necropsied to determine cause of death. The skin surrounding the injection sites is carefully examined for abnormalities and is preserved in buffered formalin for future examination. All tumors arising in the positive control group and any tumors from the experimental groups are measured, weighed, and preserved in buffered formalin. Because lungs are a frequent site of tumor metastasis, the lungs of all animals are perused and examined for metastases. Moreover, the lungs are fixed, embedded in paraffin, and sectioned for histological evaluation. Any abnormalities are noted.

Evaluation Criteria:

The presence of any tumors at the sites of injection in mice injected with NIKSTIMP1 cells indicates that these clones are tumorigenic and preferably excludes them for further development. Because tumors arise spontaneously with known frequencies in nude mice, the presence of tumors at sites other than the injection sites is anticipated and does necessarily indicate tumorigenicity of the test article. If the incidence of distant tumors in the experimental groups is not significantly higher than that observed in the negative control group or than published tumor frequencies, the results indicate that the test article does not exhibit increased tumorigenic potential. If the incidence of distant tumors in either of the experimental groups is significantly higher than that observed in the control group, the test article will be judged to have elevated tumorigenic potential.

Test NIKSTIMP1 Cells for the Presence of Viral Adventitious Agents.

Samples are also tested for the presence of known and unknown pathogens. The NIKSTIMP1 cell line chosen for creation of a camp master cell bank (Weidman Center Clinical Biomanufacturing Facility, University of Wisconsin- Madison) is screened for the presence of HPV DNA sequences using an FDA-approved test. These NIKSTIMP1 cells are preferably free of HPV DNA from the high-risk HPV subtypes 16, 18, 31, 33, 35, 39, 45, 51, 52, 56, 58, 59, and 68.

The candidate NIKSTIMP1 cell line is screened for the presence of specific viral pathogens, including HIV-1, HIV-2, HTLV-I, HTLV-II, Hepatitis B virus, Hepatitis C virus, Epstein-Barr virus, Cytomegalovirus, B19 human parvovirus, SV40, HHV-6, HHV-7, Reverse transcriptase, Bovine and Porcine viruses as outlined in FDA guidance document "Points to Consider in the Characterization of Cell Lines Used to Produce Biologicals (1993)." In addition, FDA-approved animal testing in embryonated eggs and mice is conducted to demonstrate that NIKSTIMP1 keratinocytes are free of unidentified viral adventitious agents. The NIKSTIMP1 are also tested to ensure that they are free of mycoplasma contamination as determined by Hoechst staining and broth culture.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in molecular biology, biochemistry, or related fields are intended to be within the scope of the following claims.

We claim:

1. A composition comprising a human skin equivalent comprising stratified Near-diploid Immortalized Keratinocyte (NIKS) cells adhered to a physiological substratum of dermal fibroblasts embedded within a fibrillar collagen base, said NIKS cells expressing a heterologous TIMP-1 gene and having normal cellular proliferation as compared to untransfected Near-diploid Immortalized Keratinocyte cells, wherein said gene encoding said heterologous TIMP-1 gene is operably linked to a promoter sequence that allows TIMP-1 gene expression in said human skin equivalent, wherein said promoter sequence is selected from the group consisting of a K14 promoter, an involucrin promoter, and a ubiquitin promoter.

2. A method for providing cells expressing a heterologous TIMP-1, comprising:
   a) providing Near-diploid Immortalized Keratinocyte (NIKS) cells and an expression vector comprising a DNA sequence encoding a TIMP-1 gene operably linked to a regulatory sequence;
   b) introducing said expression vector to said Near-diploid Immortalized Keratinocyte cells; and
   c) organotypically culturing said Near-diploid Immortalized Keratinocyte cells under conditions such that said cells stratify and adhere to a physiological substratum of dermal fibroblasts embedded within a fibrillar collagen base and said heterologous TIMP-1 is expressed and wherein said Near-diploid Immortalized Keratinocyte cells have normal cellular proliferation as compared to untransfected Near-diploid Immortalized Keratinocyte cells.

3. The method of claim 2, wherein said Near-diploid Immortalized Keratinocyte cells are capable of stratifying into squamous epithelia.

4. The method of claim 2, further comprising co-culturing said Near-diploid Immortalized Keratinocyte cells with cells derived from a patient.

5. A method of treating skin wounds comprising:
   a) providing a human skin equivalent comprising stratified Near-diploid Immortalized Keratinocyte cells (NIKS) cells adhered to a physiological substratum of dermal fibroblasts embedded within a fibrillar collagen base, said NIKS cells expressing a heterologous TIMP-1 gene wherein said Near-diploid Immortalized Keratinocyte cells have normal cellular proliferation as compared to untransfected Near-diploid Immortalized Keratinocyte cells, and a subject with a wound;
   b) contacting said skin wound with said human skin equivalent expressing a heterologous TIMP-1 gene under conditions such that said wound is treated.

6. The method of claim 5, wherein said contacting comprises a technique selected from the group consisting of topical application, engraftment and application of a wound dressing.

7. The method of claim 5, wherein said skin wounds are selected from the group comprising venous ulcers, diabetic ulcers, pressure ulcers, burns, and external injuries.

* * * * *

SEQUENCE LISTING

```
<160> NUMBER OF SEQ ID NOS: 4

<210> SEQ ID NO 1
<211> LENGTH: 782
<212> TYPE: DNA
<213> ORGANISM: Homo sapiens

<400> SEQUENCE: 1
aggggcctta gcgtgccgca tcgccgagat ccagcgccca gagagacacc agagaaccca      60
ccatggcccc ctttgagccc ctggcttctg gcatcctgtt gttgctgtgg ctgatagccc     120
ccagcagggc ctgcacctgt gtcccacccc acccacagac ggccttctgc aattccgacc     180
tcgtcatcag ggccaagttc gtggggacac cagaagtcaa ccagaccacc ttataccagc     240
gttatgagat caagatgacc aagatgtata aagggttcca agccttaggg gatgccgctg     300
acatccggtt cgtctacacc cccgccatgg agagtgtctg cggatacttc cacaggtccc     360
acaaccgcag cgaggagttt ctcattgctg gaaaactgca ggatggactc ttgcacatca     420
ctacctgcag tttcgtggct ccctggaaca gcctgagctt agctcagcgc cggggcttca     480
ccaagaccta cactgttggc tgtgaggaat gcacagtgtt tccctgttta tccatccct     540 gcaaactgca gagtggcact cattgcttgt ggacggacca gctcctccaa ggctctgaaa     600
agggcttcca gtcccgtcac cttgcctgcc tgcctcggga gccagggctg tgcacctggc     660
agtccctgcg gtcccagata gcctgaatcc tgcccggagt ggaactgaag cctgcacagt     720
gtccaccctg ttcccactcc catctttctt ccggacaatg aaataaagag ttaccaccca     780
gc                                                                      782

<210> SEQ ID NO 2
<211> LENGTH: 207
<212> TYPE: PRT
<213> ORGANISM: Homo sapiens

<400> SEQUENCE: 2

Met Ala Pro Phe Glu Pro Leu Ala Ser Gly Ile Leu Leu Leu Leu Trp
1               5                   10                  15

Leu Ile Ala Pro Ser Arg Ala Cys Thr Cys Val Pro Pro His Pro Gln
            20                  25                  30

Thr Ala Phe Cys Asn Ser Asp Leu Val Ile Arg Ala Lys Phe Val Gly
        35                  40                  45

Thr Pro Glu Val Asn Gln Thr Thr Leu Tyr Gln Arg Tyr Glu Ile Lys
    50                  55                  60
```

Met Thr Lys Met Tyr Lys Gly Phe Gln Ala Leu Gly Asp Ala Ala Asp
65                  70                  75                  80

Ile Arg Phe Val Tyr Thr Pro Ala Met Glu Ser Val Cys Gly Tyr Phe
                85                  90                  95

His Arg Ser His Asn Arg Ser Glu Glu Phe Leu Ile Ala Gly Lys Leu
            100                 105                 110

Gln Asp Gly Leu Leu His Ile Thr Thr Cys Ser Phe Val Ala Pro Trp
        115                 120                 125

Asn Ser Leu Ser Leu Ala Gln Arg Arg Gly Phe Thr Lys Thr Tyr Thr
    130                 135                 140

Val Gly Cys Glu Glu Cys Thr Val Phe Pro Cys Leu Ser Ile Pro Cys
145                 150                 155                 160

Lys Leu Gln Ser Gly Thr His Cys Leu Trp Thr Asp Gln Leu Leu Gln
                165                 170                 175

Gly Ser Glu Lys Gly Phe Gln Ser Arg His Leu Ala Cys Leu Pro Arg
            180                 185                 190

Glu Pro Gly Leu Cys Thr Trp Gln Ser Leu Arg Ser Gln Ile Ala
        195                 200                 205

<210> SEQ ID NO 3
<211> LENGTH: 598
<212> TYPE: DNA
<213> ORGANISM: Homo sapiens

<400> SEQUENCE: 3
cagagtcact cctgccttca ccatgaagtc cagcggcctc ttccccttcc tggtgctgct     60
tgccctggga actctggcac cttgggctgt ggaaggctct ggaaagtcct tcaaagctgg    120
agtctgtcct cctaagaaat ctgcccagtg ccttagatac aagaaacctg agtgccagag    180
tgactggcag tgtccaggga agaagagatg ttgtcctgac acttgtggca tcaaatgcct    240
ggatcctgtt gacacccaa acccaacaag gaggaagcct gggaagtgcc cagtgactta    300
tggccaatgt ttgatgctta accccccaa tttctgtgag atggatggcc agtgcaagcg    360
tgacttgaag tgttgcatgg gcatgtgtgg gaaatcctgc gtttcccctg tgaaagcttg    420
attcctgcca tatggaggag ctctggagt cctgctctgt gtggtccagg tccttccac    480
cctgagactt ggctccacca ctgatatcct cctttgggga aaggcttggc acacagcagg    540
cttttcaagaa gtgccagttg atcaatgaat aaataaacga gcctatttct ctttgcac     598

<210> SEQ ID NO 4
<211> LENGTH: 132
<212> TYPE: PRT
<213> ORGANISM: Homo sapiens

<400> SEQUENCE: 4

Met Lys Ser Ser Gly Leu Phe Pro Phe Leu Val Leu Leu Ala Leu Gly
1               5                   10                  15

Thr Leu Ala Pro Trp Ala Val Glu Gly Ser Gly Lys Ser Phe Lys Ala
            20                  25                  30

Gly Val Cys Pro Pro Lys Lys Ser Ala Gln Cys Leu Arg Tyr Lys Lys
        35                  40                  45

Pro Glu Cys Gln Ser Asp Trp Gln Cys Pro Gly Lys Lys Arg Cys Cys
    50                  55                  60

Pro Asp Thr Cys Gly Ile Lys Cys Leu Asp Pro Val Asp Thr Pro Asn
65                  70                  75                  80

Pro Thr Arg Arg Lys Pro Gly Lys Cys Pro Val Thr Tyr Gly Gln Cys

-continued

```
                85                  90                  95
Leu Met Leu Asn Pro Pro Asn Phe Cys Glu Met Asp Gly Gln Cys Lys
            100                 105                 110

Arg Asp Leu Lys Cys Cys Met Gly Met Cys Gly Lys Ser Cys Val Ser
            115                 120                 125

Pro Val Lys Ala
            130
```